United States Patent
Wilson

(10) Patent No.: US 7,794,720 B2
(45) Date of Patent: Sep. 14, 2010

(54) ISOLATED PLASMA AND METHOD FOR HYPERIMMUNISATION AND PLASMA COLLECTION

(75) Inventor: Ross Phillip Wilson, Kalbar (AU)

(73) Assignee: Plasma Ventures Pty Ltd, Kalbar, Queensland (AU)

( * ) Notice: Subject to any disclaimer, the term of this patent is extended or adjusted under 35 U.S.C. 154(b) by 713 days.

(21) Appl. No.: 10/589,931

(22) PCT Filed: Apr. 29, 2004

(86) PCT No.: PCT/AU2004/000552

§ 371 (c)(1),
(2), (4) Date: Oct. 16, 2006

(87) PCT Pub. No.: WO2005/077299

PCT Pub. Date: Aug. 25, 2005

(65) Prior Publication Data

US 2007/0248612 A1      Oct. 25, 2007

(30) Foreign Application Priority Data

Feb. 18, 2004   (AU) .............................. 2004900805

(51) Int. Cl.
*A61K 39/395* (2006.01)
*A61K 35/16* (2006.01)
*G01N 33/555* (2006.01)

(52) U.S. Cl. ................. 424/169.1; 424/241.1; 424/530; 435/7.25; 436/520; 604/6.04

(58) Field of Classification Search ........................ None
See application file for complete search history.

(56) References Cited

U.S. PATENT DOCUMENTS 3,950,512 A * 4/1976 Emery et al. .............. 424/201.1
4,965,068 A   10/1990 Stephan et al.

OTHER PUBLICATIONS

Giger U et al.; "An acute hemolytic transfusion reaction caused by dog erythrocyte antigen 1.1 incompatibility in a previously sensitized dog."; Journal of the American Veterinary Medical Association, May 1, 1995, 206(9), pp. 1358-1362.
Hale A.S., "Canine blood groups and their importance in veterinary transfusion medicine", Transfusion medicine, Nov. 1995, vol. 25, No. 6, pp. 1323-1332.
Harvath L., et al.; "Passive immunity against *Pseudomonas sepsis* during granulocytopenia", Infection and Immunity, Nov. 1976, 14 (5), pp. 1151-1155.
Natanson C. et al.; Plasma exchange does not improve survival in a canine model of human septic shock: Transfusion, Mar. 1993, 33(3) pp. 243-248.
Lee R., et al.; "Percutaneous central dual-lumen catheter for apheresis in the canine", J. Invest Surg, Nov.-Dec. 2002, 15(6), pp. 337-341.
International Preliminary Report on Patentability, issued Aug. 22, 2006, for corresponding International Application No. PCT/US2004/000552, filed Apr. 29, 2004.

* cited by examiner

*Primary Examiner*—David A Saunders
(74) *Attorney, Agent, or Firm*—Hoffman & Baron, LLP

(57) ABSTRACT

The present invention relates to isolated canine animal plasma, a method for isolating canine animal plasma, plasma obtained form an immunised or hyperimmunised canine animal and treating a canine animal with the isolated canine animal plasma. The method includes the step of selecting a canine animal having a blood group compatible with a recipient canine animal having an unmatched blood group, namely, selecting a canine animal for a blood group that does not cause plasma transfusion reaction and/or haemolysis. In one form, the method includes the step of immunising or hyperimmunising a canine animal plasma donor with one or more antigens of a canine animal pathogen. The pathogen is preferably a bacteria or virus.

13 Claims, 9 Drawing Sheets

Table 1

| DATE | VACCINE USED | DOSE |
|---|---|---|
| Introduction | Canine 5 | Full dose |
| +1 month | Canine 5 | Full dose |
| +1.5 months | J5 plus Freunds Adjuvant | 1mL* |
| +2 months | J5 plain | 1mL* |
| Collections begin +2.5 months | J5 plain | 1mL* |
| At every collection thereafter | J5 plain | 0.5mL per collection for 6 collections, then 0.25mL per colln thereafter |
|  | Canine 5 | one-half dose per collection for 6 collections, then one-quarter dose per colln therefater* |

Table 2

| Parameter | Dogs |
|---|---|
| Machine Used | Haemonetics PCS plus |
| Latham Bowl size | 150ml |
| Draw Pump Speed | 80 mL/minute |
| Return Pump Speed | 100mL/minute |
| Volume Collected | 1.2L |
| Minimum Specification: Gamma Globulins | 10g/L |
| Total Protein reading on Refractometer | 40g/L |
| Sterility Anaerobes (Thioglycollate) Aerobes (Tryptone Soy) | Sterile (no growth at 14 days) Sterile (no growth at 14 days) |
| Blood Cell Contamination minimum levels: Red Cells White Cells Platelets | <30,000 million/L <200 million/L <50,000 million/L |
| Universal Plasma Donors | Yes |
|  |  |
| Minimum Withholding Period before sale | Nil (no long incubation period viruses in dogs in Australia) |

Table 3

| Collection/Batch Number | GG bag 1 (g/L) | GG bag 2 | GG bag 3 | GG bag 4 | GG bag 5 | GG bag 6 (g/L) |
|---|---|---|---|---|---|---|
| 3 | 21 | 21 | 19 | 15 | 12 | 9 |
| 4 | 12 | 13 | 11 | 9 | 7 | 6 |
| 5 | 17 | 18 | 17 | 15 | 12 | Not collected |
| 6 | 16 | 13 | 13 | 12 | 9 | Not collected |

Table 4

| Batch | Date | Sterility | Cell Counts (x million/L) | Potency GG |
|---|---|---|---|---|
| 1 | 13/12/00 | Thioglyc-no growth<br>Tryptone-no growth | Red- 30,000<br>White-200<br>Platelet-8,000 | 8g/L |
| 2 | 4/1/01 | Thioglyc-no growth<br>Tryptone-no growth | Red - 20,000<br>White - 200<br>Platelets - 10,000 | 9g/L |
| 3 | 8/2/01 | Thioglyc-no growth<br>Tryptone-no growth | Red - 28.000<br>White - 61<br>Platelets - 9,400 | 12g/L |
| 4* | 16/2/01 | Thioglyc-no growth<br>Tryptone-no growth | Red - 74,000<br>White - 77<br>Platelets - 70.700 | 9g/L |
| 5 | 1/3/01 | Thioglyc-no growth<br>Tryptone-no growth | Red - 11,000<br>White - 6<br>Platelet - 17,400 | 9g/L |
| 6 | 2/3/01 | Thioglyc-no growth<br>Tryptone-no growth | Red - 2,000<br>White - 3<br>Platelet - 1,670 | 13g/L |
| 7* | 8/3/01 | Thioglyc-no growth<br>Tryptone-no growth | Red - 20,000<br>White - 1<br>Platelet - 8,950 | 12g/L |
| 8* | 21/3/01 | Thioglyc-no growth<br>Tryptone-no growth | Red - 9,000<br>White - 9<br>Platelet - 44,500 | 10.5g/L |
| 9* | 27/2/02 | Thioglyc-no growth<br>Tryptone-no growth | Red - 10,000<br>White - 100<br>Platelet - 19,000 | 11g/L |
| 10* | 27/3/02 | Thioglyc-no growth<br>Tryptone-no growth | Red - 12,000<br>White - 154<br>Platelet - 26,000 | 12g/L |

* following immunization of dog from batch 1

Table 5

| Parameter | Measured by | Limits | Remedy if outside limits |
|---|---|---|---|
| Mucus membrane colour | Observation | Pale<br>Normal pink<br>Congested<br>Blue (Cyanosis) | Discontinue collection<br>Continue collection<br>Slow rate of I/V fluid drip<br>Check and correct oxygen flow |
| Capillary Refill Time | Observation after digital pressure on gums | <3 seconds | Increase rate of I/V fluid drip |
| Heart Rate | Counting, from Oesophageal Stethoscope | Too Slow (<50bpm)<br><br>Too Fast | Administer another dose of Atropine at 0.5mg/Kg body weight<br><br>Increase flow rate of Halothane, if depth of anaes too light<br>Decrease rate of I/V fluids if depth of anaes OK |
| Depth of anaesthesia | -Response to painful stimulus<br>-eye position<br>-blink<br>-pupil | Between respiratory arrest and climbing off table | Increase Halothane flow if too light, decrease if too deep, and wash lungs with pure oxygen |
| Respiratory Rate | Counted by/on listening to Oesoph steth | Lower limit 6<br><br>Upper 20 | -decrease Halothane flow administer resp stimulant<br><br>-increase Halothane flow to deepen anaesthetic |

Table 6

| Alpha globulins | 5-16 g/L |
|---|---|
| Beta globulins | 6-12 g/L |
| Gamma globulins | 5-18 g/L |
|  |  |
| TOTAL GLOBULINS | 27-44 g/L |

Table 7

| Bag number | GG (g/L) | TP reading (g/L) | Bag number | GG (g/L) | TP reading (g/L) |
|---|---|---|---|---|---|
| 4/6 | 7.0 | 35 | 5/1 | 15.4 | 55 |
| 5/5 | 11.0 | 48 | 6/1 | 15.0 | 53 |
| 6/5 | 6.5 | 40 | 7/1 | 11.0 | 49 |
| 7/6 | 6.5 | 33 | 8/1 | 13.0 | 55 |
| 8/6 | 5.5 | 26 | 10/1 | 14.0 | 4.2 |
| 10/6 | 5.5 | 1.9 | | | |

Table 8

| Batch | Bag number | GG concentration (g/L) |
|---|---|---|
| 3 | 1 | 21 |
| | 2 | 21 |
| | 3 | 19 |
| | 4 | 15 |
| | 5 | 12 |
| | 6 | 9 |
| 4 | 1 | 12 |
| | 2 | 13 |
| | 3 | 11 |
| | 4 | 9 |
| | 5 | 7 |
| | 6 | 6 |
| 5 | 1 | 17 |
| | 2 | 18 |
| | 3 | 17 |
| | 4 | 15 |
| | 5 | 12 |
| 6 | 1 | 16 |
| | 2 | 13 |
| | 3 | 13 |
| | 4 | 12 |
| | 5 | 9 |

Table 9

| No. | Patient | Date of Admission | Presenting Condition | Outcome |
|---|---|---|---|---|
| 1 | "Gremlin" Bowler | 9/7/01 | Severe Enteritis | Died |
| 2 | "Jemma" Browne | 29/5/01 | Idiopathic Pericarditis | Successful with surgery |
| 3 | "Kirra" Carr | 19/2/01 | Parvovirus Infection | Successful with much shortened course of treatment and hospitalization |
| 4 | "Molly" Cooper | 15/2/02 | Acute Pancreatitis | Died with severe liver damage |
| 5 | "Jazzie" Edmondson | 9/6/01 | Acute Pancreatitis | Successful |
| 6 | "Sean" Fainges | 14/12/00 | Black Snake Bite (multiple) | Successful (unable to use antivenom) |
| 7 | "Angel" Reid | 27/10/01 | Acute Pancreatitis | Successful |
| 8 | "Meg" Richardson | 4/6/01 | Coagulopathy | Successful |
| 9 | "Squeak" Ruhland | 28/9/01 | Envenomation (unknown source) | Died |
| 10 | "Jessie" Titmarsh | 27/2/01 | OP poisoning – secondary enteritis | Successful |
| 11 | "Max" Wales | 15/6/01 | Acute polyradiculoneuritis | Successful |
| 12 | "Jerry" Watson | 2/2/01 | Acute Pancreatitis | Successful |
| 13 | "Zoe" West | 30/4/01 | Pulmonary Haemorrhage (coagulopathy) | Successful |
| 14 | "Blaze" Zimmermann | 30/1/02 | Acute Pancreatitis – Parvovirus/Enteritis | Successful |
| | | | | |

Table 10

| Type of case | Number | Outcome |
|---|---|---|
| Pancreatitis | 5* | 4/5 success |
| Coagulopathy | 4 | 3/4 success |
| Parvovirus Infection /Severe Enteritis | 4* | 3/4 success |
| Miscellaneous | 1 | 1/1 success |
| | 1 | 1/1 success |

ISOLATED PLASMA AND METHOD FOR HYPERIMMUNISATION AND PLASMA COLLECTION

CROSS-REFERENCE TO RELATED APPLICATIONS

This application is the National Stage of International Application No. PCT/AU2004/000552, filed Apr. 29, 2004, which claims the benefit of Australian Application No. 2004900805, filed Feb. 18, 2004.

FIELD OF THE INVENTION

THIS INVENTION relates to isolated plasma, a method for hyperimmunisation and plasma collection from canine animals.

BACKGROUND OF THE INVENTION

Prior to the present invention, canine plasma available to veterinarians for use in canine patients has been "homemade" plasma typically made by veterinarians. This "homemade" plasma is produced as follows: a veterinarian collects whole blood from a donor dog; the collected blood is stored refrigerated for a three week period (the viable life span for red blood cells) and is thereby available for use, for example in a blood transfusion; and after the three week period, the collected blood is transported to a canine blood bank. At the blood bank the blood is centrifuged at a low speed (2,000 rpm, the maximum speed achievable for a 500 g bag of blood), causing the blood cells to "settle" and thereby roughly separating the plasma at the top of the bag from the blood cells at the bottom. The plasma is then siphoned off the top into another bag and frozen for later clinical use. The plasma separation step may also be performed at the time the blood is collected The results achieved using dog plasma made by the above method have been only moderately satisfactory. Using plasma made in accordance with the above method exposes a patient to considerable potential for adverse treatment, including for example: transfusion reactions (fatal rupture of either the donor's or the recipient's red blood cells in the recipient's blood stream, known as Haemolysis, which is caused by the presence of unacceptable numbers of red cells in the donated plasma, or antibodies to donor red cell blood group in recipient's plasma, or antibodies to recipient red cell blood group in donor's plasma); transmission of disease, because the blood donors are frequently of either unknown or poor health; transfusion of plasma that is not sterile because of poor collection techniques, and possibly comprising contaminating bacteria, bacterial fragments or endotoxins (released when bacterial cells rupture), which can cause fatal infections/reactions in recipient patients. Also, homemade plasma preparations are not always be available, because of poor shelf life and labour intensive nature of production.

The use of plasma therapy in veterinary medicine is predominately in equine medicine, especially in referral centres, under the supervision of specialist equine veterinary practitioners. Plasma therapy has also been a treatment in other large animals including camelids such as Alpacas and Llamas. Plasma collection in large animals such as equine is less problematic compared with canine in part because of larger body mass and blood volume and the passive nature of the collection animal.

There remains a need for a safe and reliable method for collecting plasma from canine animals and isolated plasma that is reliable, safe and efficacious for use as a therapeutic agent.

SUMMARY OF THE INVENTION

It is an object of the invention to provide an alternative or improvement to the abovementioned background art.

The inventors have developed a method for isolating plasma from a canine animal and a hyperimmunised canine animal and plasma isolated by the methods.

A canine or canine animal comprises any member of the family Canidae, including, dogs (domestic or wild), wolves, jackals, hyenas, coyotes and foxes.

In a first aspect, the invention provides a method of isolating plasma from a canine animal including the steps of:

(I) selecting a canine animal having a blood group compatible with a recipient canine animal having an unmatched blood group;

(II) collecting blood from the canine animal; and (III) isolating plasma from blood collected in step (II).

A blood group of a canine that is compatible with a recipient canine animal having an unmatched blood group means that isolated plasma from the canine animal will not cause a substantial plasma transfusion reaction and/or haemolysis in the recipient canine animal.

Preferably, the canine animal is selected for a phenotype lacking at least one Dog Erythrocyte Antigen.

More preferably, the canine animal is negative for Dog Erythrocyte Antigen 1.1.

Even more preferably, the canine animal is further negative for Dog Erythrocyte Antigen 1.2.

Still more preferably, the canine animal is further negative for Dog Erythrocyte Antigen 7.

The canine animal may further be negative for DEA 3, DEA 5 DEA 6 and/or DEA 8.

Preferably, the canine animal is further selected for a phenotype lacking anti-globulin antibodies.

In a preferred form of the first aspect, the method further includes the steps of:

(a) inserting a blood collecting catheter into a vein of the canine animal;

(b) attaching the blood collecting catheter to a cell separator capable of separating blood into an isolated plasma component and an isolated blood cell component;

(c) collecting blood from the canine animal via the blood collection catheter;

(d) separating the blood into the isolated plasma component and the isolated blood cell component;

(e) collecting the isolated plasma component;

(f) stopping the collecting of blood;

(g) returning the blood cell component to the canine animal; and (h) repeating steps (c)-(g).

In one form, step (h) is repeated until a total plasma protein concentration in the isolated plasma component is equal to a reference total plasma concentration.

In another form, step (h) is repeated until a gamma globulin concentration in the isolated plasma component is equal to a reference gamma globulin concentration.

Preferably, the cell separator comprises a centrifuge and/or membrane comprising a suitable pore size for separating blood cells from plasma.

The centrifuge preferably comprises a rotating centrifuge bowl whereby the isolate plasma component is collected from an upper portion of the rotating centrifuge bowl.

Preferably, collecting of blood is stopped when blood cells are detected in the isolated plasma component.

The blood cells are preferably detected by visual inspection by an operator and/or by an automated cell analyser.

The blood cells preferably comprise red blood cells, white blood cells and/or platelets.

Preferably, the isolated plasma component comprises less than 30,000 million red blood cells per liter, less than 200 million white blood cells per liter and/or less than 50,0000 million platelets per liter.

Preferably, the reference total plasma protein concentration is selected from the group consisting of: 40 g/L, 35 g/L, 30 g/L and 25 g/L.

More preferably, the reference total plasma protein concentration is 25 g/L.

Preferably, the reference gamma globulin plasma concentration is selected from the group consisting of: 10 g/L, 12 g/L, 15 g/L and 18 g/L.

More preferably, the reference gamma globulin plasma concentration is 10 g/L.

In one form, the method preferably further includes the step of anaesthetising the canine animal prior to collecting blood.

Anaesthetising preferably includes administering an anaesthetic inducing agent selected from the group consisting of: propofol, thiopental sodium and other ultra short-action barbiturates.

The method may further include the step of administering halothane and oxygen to the canine animal after administering the anaesthetic inducing agent.

The method may still further include the step of administering to the canine animal prior to administering the anaesthetic inducing agent a pre-medication agent capable of: calming, drying salivary secretions, maintaining blood pressure and/or maintaining pulse rate of the canine animal.

The pre-medication agent is preferably acetylpromazine maleate and atropine sulphate.

The method may still further include the step of administering isotonic saline to the canine animal via an intravenous catheter prior to, during and/or after collecting blood from said canine animal.

In one form of the invention, the canine animal is immunised or hyperimmunised prior to isolating plasma as described herein.

In a second aspect, the invention provides a method of producing hyperimmunised canine animal plasma including the steps of:

(1) selecting a canine animal having a blood group compatible with a recipient canine animal having an unmatched blood group;

(2) administering to the canine animal at least one antigen thereby inducing an immune response in said canine animal;

(3) administering to said canine animal at least one same antigen(s) administered in step (2) during said immune response; and (4) isolating plasma from said canine animal.

The term "induced immune response" and "immune response" comprises stimulation of an immune response in an animal, preferably a mammal, more preferably a canine animal, for example following administration of an antigen(s), such as a vaccine, wherein B lymphocytes of the canine animal produce an increased quantity of an antibody specific to the antigen(s). The immune response need not provide protective immunity against a pathogen.

Preferably, the canine animal is characterised by a phenotype negative for at least one Dog Erythrocyte Antigen.

Preferably, the canine animal is characterised by a phenotype negative for Dog Erythrocyte Antigen 1.1.

More preferably, the canine animal is further characterised by a phenotype negative for Dog Erythrocyte Antigen 1.2

Even more preferably, the canine animal is further characterised by a phenotype negative for Dog Erythrocyte Antigen 7.

Preferably, the canine animal is characterised by a phenotype negative for anti-globulin antibodies.

Preferably, the isolated plasma comprises a gamma globulin concentration greater than 10 g/L.

More preferably, the isolated plasma comprises a gamma globulin concentration greater than 15 g/L.

Even more preferably, the isolated plasma comprises a gamma globulin concentration greater than 18 g/L.

Still more preferably, the isolated plasma comprises a gamma globulin concentration greater than 20 g/L.

The method preferably includes the step of administering at least one of the same antigen(s) two or more times while the immune response is induced in the canine animal.

More preferably, the at least one of the same antigen(s) is administered five or more times while the immune response is induced in the canine animal.

Even more preferably, the at least one of the same antigen(s) is administered ten or more times while the immune response is induced in the canine animal.

It will be appreciated that the number of times a same antigen(s) may be administered may be determined by a person skilled in the art. Accordingly, the antigen(s) may be administered once, twice, 3, 5, 10, 15, 20, 25, 30, 40, 50 or more times.

The antigen(s) are preferably administered at weekly intervals.

In one form, the antigens(s) comprises one or more vaccine.

The vaccine preferably comprises a living attenuated virus.

Preferably, the antigen(s) are antigens selected from the groups consisting of those obtainable from: distemper virus, canine adenovirus type 2 (CAV2), canine parvovirus type 2 (CPV2), canine parainfluenza virus, *Bordetella bronchiseptica*, *E. coli*, or respective components thereof.

Preferably, the *E. coli* is heat killed.

Preferably, the *E. coli* is *E. coli* J5.

The component of *E. coli* preferably comprises lipopolysaccharide and/or oligosaccharide.

Other canine viruses include: canine adeno-associated virus, canine adenovirus 1, canine calicivirus, canine cornavirus, canine herpesvirus, canine minute virus and canine papillomavirus.

A component comprises a peptide, nucleic acid, polysaccharide, monosaccharide, cell membrane and the like.

The vaccine may comprise one or more intact pathogen, pathogen extract, nucleic acid and/or peptide.

Suitably, the *E. coli* is a component of an anti-endoxin vaccine.

In a third aspect, the invention provides isolated canine animal plasma isolated in accordance with the method of the first aspect.

In a fourth aspect, the invention provides isolated canine animal plasma obtained from a canine animal hyperimmunised in accordance with the method of the second aspect.

In a fifth aspect, the invention provides isolated canine animal plasma comprising at least one immunoglobulin capable of binding to a gram negative bacteria or component thereof.

Preferably, the gram negative bacteria or component thereof is *E. coli*.

More preferably, the *E. coli* is *E. coli* J5.

The component of the *E. coli* is preferably lipopolysaccharide, oligosaccharide and/or a respective component thereof.

The isolated canine animal plasma of the fifth aspect preferably further comprises at least one immunoglobulin capable of binding an additional canine animal pathogen.

Preferably, the canine pathogen is an internal pathogen.

The canine animal pathogen is preferably selected from the group consisting of: a virus, parasite and bacteria.

The canine animal pathogen is preferably selected from the group consisting of: distemper virus, canine adenovirus type 2 (CAV2), canine parvovirus type 2 (CPV2), canine parainfluenza virus and *Bordetella bronchiseptica*.

The isolated canine animal plasma of the invention preferably comprises a gamma globulin concentration of at least 10 g/L.

More preferably, the gamma globulin concentration is at least 12 g/L.

Even more preferably, the gamma globulin concentration is at least 15 g/L.

Still more preferably, the gamma globulin concentration is at least 18 g/L.

Preferably, the isolated canine plasma further comprises less than about 50,000 million red blood cells per liter, less than about 500 million white blood cells per liter and/or less than about 100,0000 million platelets per liter.

More preferably, the isolated canine plasma further comprises less than about 40,000 million red blood cells per liter, less than about 300 million white blood cells per liter and/or less than about 75,0000 million platelets per liter.

Even more preferably, the isolated canine plasma further comprises less than about 35,000 million red blood cells per liter, less than about 250 million white blood cells per liter and/or less than about 60,0000 million platelets per liter.

Still more preferably, the isolated canine plasma further comprises less than about 30,000 million red blood cells per liter, less than about 200 million white blood cells per liter and/or less than about 50,0000 million platelets per liter.

The isolated canine plasma may still further preferably comprises less than about 20,000 million red blood cells per liter, less than about 100 million white blood cells per liter and/or less than about 10,0000 million platelets per liter.

In a sixth aspect, the invention provides a method for treating or improving health of a canine animal of a condition including the steps of administering to the canine animal isolated canine animal plasma of the invention.

Treating encompasses a partial and complete recovery from the condition.

The condition is preferably selected from the group consisting of: parvovirus infection, lack of passive transfer of antibodies to a canine pup, hypoprotinaemia, glomerulonephritis, shock, fluid therapy, congenital clotting disorders, thrombocytopenia, vitamin K deficiency, haemphilia, disseminated intravascular coagulation, pancreatitis, reduced blood coagulation, infection, surgery, tissue injury and destruction, pyometron, poisoning, snake envenomation, advanced blood loss and severely debilitating infections.

Reduced blood coagulation may be a result of poisoning, disseminated intravascular coagulation and/or haemophilia Preferably, the isolated canine animal plasma is administered in range of 2-15 mL/Kg weight of the canine animal per hour.

More preferably, the isolated canine animal plasma is administered in a range of 3-12 mL/Kg weight of the canine animal per hour.

Even more preferably, the isolated canine animal plasma is administered in a range of 5-10 mL/Kg weight of the canine animal per hour.

It will be appreciated that although one form of the invention relates to isolated hyperimmune canine animal plasma, the isolated plasma need not be obtained from a hyperimmunised canine donor. Plasma isolated from a non-immunised or non-hyperimmunised canine donor obtained by the method of the invention has many advantages over known canine animal plasma as discussed herein. For example, the isolated canine animal plasma prepared by the method of the invention is preferably obtained from a canine donor of a blood type or blood group that is compatible with a recipient canine animal having an unmatched blood type and accordingly does not cause a plasma transfusion reaction and/or haemolysis. Also, plasma may be isolated from a canine donor that has been immunised by standard methods known in the art and not hyperimmunised as described herein. For example, the canine donor may be immunised once for one or more antigens. When a canine donor is immunised rather than hyperimmunised, the plasma preferably is isolated while the immune response is induced. Preferably, an antibody titre for antibodies capable of binding to the antigen(s) is maximal or near maximal.

It will also be appreciated that although the method preferably relates to isolation of canine animal plasma, serum and other blood products may be prepared from the isolated canine animal plasma. Also, the blood cells separated from the canine and returned to the donor may instead be retained, for example for use in transfusion of packed red blood cells.

Throughout this specification unless the context requires otherwise, the word "comprise", and variations such as "comprises" or "comprising", will be understood to imply the inclusion of the stated integers or group of integers or steps but not the exclusion of any other integer or group of integers.

BRIEF DESCRIPTION OF THE FIGURES AND TABLES

In order that the invention may be readily understood and put into practical effect, preferred embodiments will now be described by way of example with reference to the accompanying figures and tables.

TABLE 1 shows an example of a hyperimmunisation schedule;

TABLE 2 shows parameters for collecting plasma from a canine;

TABLE 3 shows gamma globulin concentrations of plasma collected from non-hyperimmunised canines;

TABLE 4 shows an example of results for sterility, cell counts and gamma globulin concentration (potency) for isolated plasma;

TABLE 5 shows parameters, method of measurement, acceptable limits and remedy if outside acceptable limits when assessing level anaesthesia;

TABLE 6 shows levels of normal blood concentrations of alpha, beta, gamma and total globulins in dog;

TABLE 7 shows a comparison between gamma globulin concentration and total protein concentration (g/L);

TABLE 8 shows a decline in gamma globulin concentration in sequential plasma collection bags during plasma isolation;

TABLE 9 shows treatment of dogs with non-hyperimmune isolated canine plasma made in accordance with the invention; and TABLE 10 summarises data in table 9 by treatment of the indicated condition.

DETAILED DESCRIPTION OF THE INVENTION

Definitions

Unless defined otherwise, all technical and scientific terms used herein have a meaning as commonly understood by those of ordinary skill in the art to which the invention belongs. Although any method and material similar or equivalent to those described herein can be used in the practice or testing of the present invention, preferred methods and materials are described. For the purpose of the present invention, the following terms are defined below.

"Plasma" refers to a liquid uncoagulated component of blood comprising proteins, including antibodies and clotting factors.

"Plasma Therapy" means a process of administering plasma or plasma-based product to an individual to increase an amount of one or more serum protein(s) in the blood of a recipient. The serum protein(s) may include antibodies.

Figure 1:
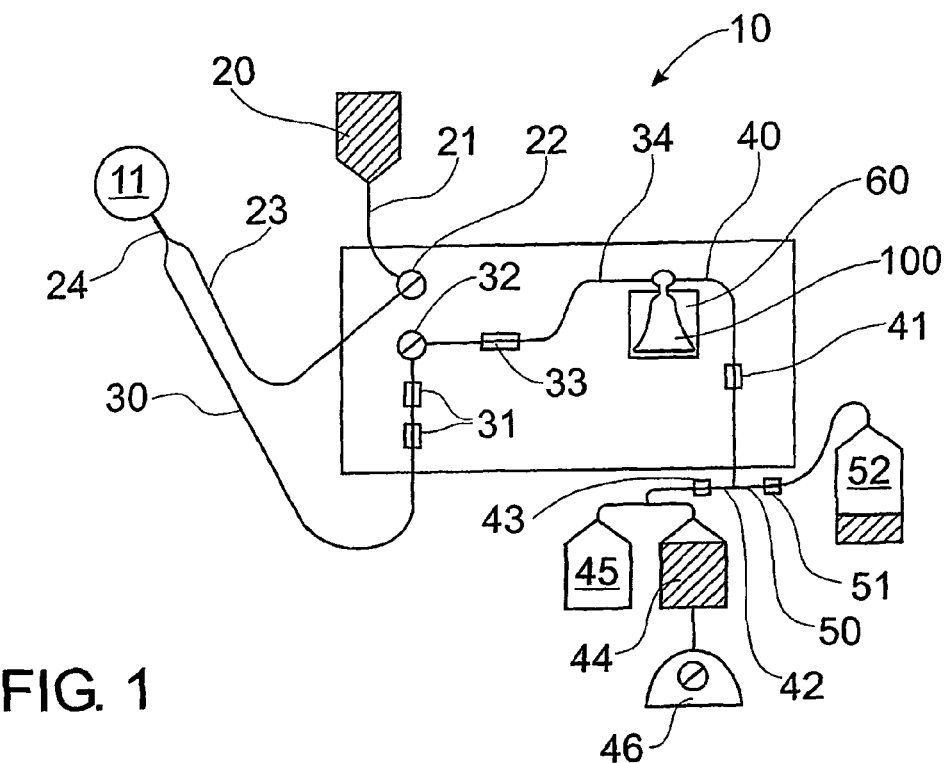
FIG. 1 is a diagram generally illustrating components of a preferred form of a plasma collection apparatus (e.g. apheresis machine)

"Plasmapheresis" is a process in which plasma is separated and removed from blood cells of an individual using, for example, a cell separator. The separator may comprise a centrifuge and/or membrane with a pore size suitable to separate blood cells from plasma. The blood cells are returned to the individual and the plasma is collected and replaced within the donor's body with other fluids, by the normal compensatory mechanisms in such situations. Medication to keep the blood from clotting (an anticoagulant) may be mixed with the donor blood at the venipuncture site during the plasmapheresis. The cell separator of present invention is a modified version of a cell separator used by human blood banks, for example a Haemonetics PCS Plus plasma collection machine. The cell separator of the invention comprises modified software and hardware compared to a commercially available version. Also, a sterile, single use "drop-in" collection kit has been developed and is used in the present invention. Components of the collection kit are shown in FIG. 1 as items 20, 21, 23, 30, 34, 40 and 100. Plasma collected according to the method of the present invention is sterile (sterility is tested for each batch of plasma produced).

"Hyperimmune plasma" refers to plasma comprising an increased concentration of gamma globulins, preferably all gamma globulins and in particular antibodies capable of binding to a specific antigen, when compared to a non-immunised animal. Hyperimmune plasma is obtainable from a donor that has been subject to a hyperimmunisation regimen comprising administration of an antigen, including commercial and custom-made vaccines, to thereby elicit antibodies that target specific antigens in the recipient. In response to hyperimmunisation, donors may accumulate an antibody concentration in their bloodstream 2-3 times higher than those of normal animals.

Donor Canine Animal Selection

At least two aspects are considered when selecting a donor canine animal, namely, suitability of the donor with respect to blood grouping or blood type and suitability with respect to the presence or absence of Virus, or other blood-borne organisms, in the donor's plasma.

Blood Grouping Compatibility

Main factors that may be present in the blood stream of dogs, which would appear to prevent them from being suitable as plasma donors include: (a) Dog Erythrocyte Antigens—in the plasma and (b) anti-globulin antibodies—on the surface of the red cells and in the plasma.

(a) Dog Erythrocyte Antigens (DEA)

Dog Erythrocyte Antigens are cell membrane receptors, comprising glycoproteins and glycolipids on the surface of the red cells, which account for 70-80% of immune-mediated transfusion reactions in the dog. In health, these receptors are responsible for cell recognition—self versus nonself. In disease, they may serve as receptors for antibody, or markers in disease occurrence. Currently their description is reliant on polyclonal antibody serology (Hale, 1995, "Canine Blood Groups and their importance in Veterinary Transfusion Medicine", Veterinary Clinics of North America: Small Animal Practice, 25 1323-1332).

This internationally accepted Canine Blood Group System, The "DEA" system (Dog Erythrocyte Antigen) is based on several DEA's that can be found in dogs—1.1, 1.2, 3, 4, 5, 6, 7 and 8. These blood groups are independently inherited (Harrell and Christensen, 1995, "Canine Transfusion Reactions and their Management", Veterinary Clinics of North America: Small Animal Medicine, 25 1333).

Blood transfusions in veterinary practice are often indicated. Such indications include: acute haemorrhage, coagulopathies, such as with haemophilia (Von Willebrand's Disease—Hereditary Haemophilia) and accidental poisoning with Rodenticides, where severe loss of blood occurs and non cross-matched blood transfusions are also a very common practice in veterinary medicine. Non cross-matched blood transfusions has occurred because of: a lack of a suitable, easy, and rapid cross-matching diagnostic tool, a need for blood transfusion in an emergency situation—no time to do a cross-match, laziness on the part of the treating veterinarian and ignorance on the part of the treating veterinarian.

Unmatched transfusions of incompatible blood into a recipient can result in the formation (in the recipient) of antibodies to the donor's red cell blood type. This would occur about 7 days after the incompatible blood transfusion, and the antibodies would persist for life. A dog which develops antibodies to the blood group of the donated blood, would suffer an immediate acute haemolytic transfusion reaction, upon receiving further blood of the same blood group.

DEA1.1 and 1.2 are the most significant blood factors in the dog. Both are highly antigenic, but antibody to DEA1.1 is the primary haemolytic factor in canine transfusion medicine. Although all of the blood group antigens are capable of stimulating formation of isoantibodies, DEA1.1 has the greatest stimulation potential. Naturally occurring antibodies to DEA1.1 have not been found. The consequence of this finding is that first-time transfusion reactions do not occur. However, if a DEA1.1 negative dog is exposed to DEA1.1 positive erythrocytes, a strong haemolysin can result. On second exposure, an immune mediated haemolytic transfusion reaction results, causing removal of transfused red cells in less than 12 hours. In addition to uncrossmatched, incompatible, untyped transfusion, pregnancy can also cause production of antibody against DEA1.1 positive red cells 25% of the time. Clinically significant reactions to DEA 1.2 may occur, but are less severe than reactions to DEA1.1 antigen.

DEA7 may be a factor in transfusion reactions, and is a naturally occurring isoantibody. This DEA7 antibody is naturally occurring in 20-50% of all dogs, but is considered to have very low clinical significance. These reactions are usually delayed (up to 7 days post transfusion), and show merely as a reduced half-life of the transfused red cells. Harrell and Kristensen, supra report that naturally occurring antibodies to DEA7 occur in the dog, but the actual incidence is yet to be accurately determined. Transfusion Reactions to DEA7 incompatible blood have not been documented. However it has been shown that chromium tagged DEA7 positive erythrocytes are destroyed in 4-5 days after transfusion into DEA7 negative dogs. The remaining Antigens are considered to cause clinically insignificant transfusion problems (Harrell and Christensen, supra).

Ideally, all transfused blood should be DEA 1.1 negative. Certain dog breeds such as Greyhounds are particularly suitable as blood donors because of a low frequency of DEA 1.1, and DEA 1.2 and DEA 7 positive blood group antigens ("Rapid Vet-H" Blood Group Determination Assay for Canine DEA 1.1—dmslaboratories, inc. Kansas USA—product enclosure).

It is estimated that 40% of all dogs are DEA 1.1 antigen positive (not including Greyhounds). Therefore the potential of an unmatched DEA 1.1 positive blood transfusion occurring is 40%—which would sensitize all DEA 1.1 negative recipient dogs.

In summary, a dog that is DEA 1.1 positive can receive DEA 1.1 positive and DEA 1.1 negative blood. However a DEA 1.1 negative dog cannot receive DEA 1.1 positive blood in a transfusion. This will only be a problem, if the DEA 1.1 negative recipient has received previous DEA 1.1 positive blood (via an unmatched blood transfusion of DEA 1.1 positive blood), and therefore has antibodies to DEA 1.1 positive red cells present in its plasma.

A commercially available test for the DEA 1.1 antigen, the "Rapid Vet-H test" (Jain, 1986, Schalm's Veterinary Haematology, Fourth Edition, pages 73-75) can screen dogs for the presence of the DEA 1.1 antigen (DEA 1.1 "positive" dogs).

As used herein, a DEA 1.1 negative dog is a universal donor and a DEA 1.1 positive dog is a universal recipient. It will be appreciated that that the above references refer to "Blood Transfusions" not "Plasma Transfusions". However, the present inventor has discovered that because the anti-DEA 1.1 antibody resides in the plasma, a plasma transfusion of DEA 1.1 positive plasma still represents a potential threat to a DEA 1.1 negative recipient (patient) dog.

(b) Anti-Globulin Antibodies

Anti-globulin antibodies may be detected using the Coombs test. The Coombs Test detects anti-globulin antibodies on the surface of the patient's red cells (which means that these antibodies would, in theory, possibly also be present in the plasma), see for example Jain, 1986, supra. The Coomb's Test is primarily used to detect dogs with a tendency towards developing Auto Immune Haemolytic Anaemia (AIHA), or dogs possibly suffering from AIHA.

There are two types of Coomb's Test: a Direct Coomb's Test that is used to detect anti-globulin antibodies on a surface of red cells and an Indirect Coomb's Test that is used to detect anti-globulin antibodies in plasma or serum, or eluates from the red cells.

According to Jain et al (Jain et al, 2000, Veterinary Hematology Fifth Edition, page 804), the Indirect Coomb's test is not considered valid for use in veterinary species, because of the low incidence of non-cell-bound autoantibody (ie free autoantibody in the plasma). However, if small numbers of red cells were to be suspended in the plasma, the possibility for adverse reactions to transfusion of that plasma exists. It is the inventor's experience that significant numbers of red cells can be present in plasma before the plasma takes on a "pinkish" coloration—well above acceptable or maximum Quality Control limits, outlined herein.

Accordingly, a plasma donor canine animal that is negative for the "RapidVet-H" card test for DEA1.1 will also be tested with the Direct Coomb's Test. Preferably, the donor canine is selected when negative to both tests.

Acute Viral Infections

Main viruses, which infect dogs in Australia, are those for which a readily available, effective, registered, commercial vaccine is already being marketed to veterinarians in Australia. Viraemia occurs with these viruses in the viral replication phase of the infection, until the host's immune system (conferred by vaccination) is activated and eventually the virus is brought under control by this response and the virus is eliminated.

Many Veterinary Pharmaceutical Companies produce such products (see for example MIMS IVS Annual 2002—according to this publication, the following companies produce a "five way" Canine Vaccine, various forms and mixtures of live and killed virus: Virbac (Australia) Pty Ltd, CSL Limited, Fort Dodge Australia Pty Ltd). That is, a vaccine which comprises all of the following viral diseases: Canine Distemper, Infectious Canine Hepatitis (canine adenovirus types 1 and 2), Canine Parvovirus Infection, Canine Cough (or Kennel Cough, as it was formerly known) due to infection by the bacteria *Bordetella bronchiseptica* or infection by the canine Parainfluenza virus-2 and Persistent Viruses.

There are, potentially two viruses belonging to families known to cause persistent infections—canine herpes virus and canine retrovirus.

Canine Retrovirus

Although several groups of investigators claim to have isolated retroviruses from dogs, it appears that they have not isolated the same virus.

Canine cases involving retroviruses, or evidence of retroviral infection (such as the detection of reverse transcriptase activity) have been detected/isolated from dogs: only seen overseas, only seen in dogs which were already severely ill and/or immunosuppressed, such as those suffering from: chronic diarrhoea with splenomegaly, chronic parvovirus infection, leukemia and other cancers such as: granulocytic neoplasm, including: lymphosarcoma and malignant lymphoma.

Accordingly, it is unlikely that a plasma donor dog in good health would be carrying an exogenous, pathogenic retrovirus.

Canine Herpes Virus

An estimated prevalence of infection in Australia is about 20 and 40%. Accordingly, a risk of transmitting canine herpes virus in a blood product obtained from an adult dog would be extremely low or nil. If the donor dog was in fact infected with the virus and it was healthy at the time of collection, the virus would be in its latent state and would not be present in the blood of the animal.

Other Acute Viruses for which there are Presently No Available Vaccines

Such viruses include Togaviruses, Flaviviruses, Rotaviruses, Reoviruses and Canine Coronavirus. None of these viruses have viraemic stages, and therefore represent no risk to recipients of plasma collected from donor animals so infected. Such infected donors would also be showing some signs of illness during the acute infection stage with these viruses.

Bearing in mind all of the above, and considering that in one embodiment donor dogs will be hyperimmunized with the above stated, commercially available vaccine(s), it is argued that there will be no need for any viral screening of potential donor dogs, before entry into the plasma collection program, and as an ongoing process. This argument is strengthened also by the absence of any other virus, especially those with a long incubation period, that are capable of causing a viraemia.

There would be no need for testing for the viruses listed above, for which there are commercially available vaccines, simply because our dogs will already be "over-vaccinated" for those diseases. This would mean that the dogs would already have a strong antibody titre, to these five infectious agents, in their plasma, which would complicate any serological test results—difficult to differentiate between natural infection antibody versus vaccine induced antibody. The high antibody level would not only deliver the dogs a high level of protection against infection from these agents, but also make it impossible to detect any changes in antibody titre, attributable only to the particular infectious agent, and inferring whether the changes were caused by actual infection or by the vaccination regime.

In other words, the vaccination program would "muddy the waters", when trying to differentiate between antibodies induced by vaccination or infection, which is very unlikely, given the efficacy of the vaccines, even at one booster dose per year, let alone hyperimmunization. This confusion is also attributed to the fact that all viral components of the vaccines are actually living attenuated viruses. These would give rise to the production of antibodies, in the host, which would be indistinguishable to those produced as a result of active, naturally acquired infection.

Miscellaneous Blood-Borne Agents

There are two agents, falling into this category in Queensland, Australia—*Babesia canis* and *Ehrlichia platys*.

*Babesia canis* infection is mainly seen in dogs that live, or have lived in or around Townsville, in northern Queensland (Seddon, 1966, Diseases of Domestic Animals in Australia, Part 4, Protozoan and Virus Diseases, Commonwealth Department of Health). It is a protozoal parasite of red blood cells, spread by the bite of the brown dog tick *Rhipicephalus sanguineus*. The infection causes red cell breakdown, which causes thrombocytopenia. The infection is usually detected by microscopic examination of a stained thin blood smear. Because of the nature of this infection (parasite of the red cells) and the location of most infected dogs in Queensland, *Babesia canis* infection is not considered to be a high priority test, to be applied to our potential plasma donor dogs. Nevertheless, this pathogen may be tested.

*Ehrlichia platys* infection is an obligate intracellular Rickettsial organism, which only infects the platelets in the blood stream of dogs, causing a cyclical, infectious thrombocytopaenia, and is transmitted by the bite of *Rhipicephalus sanguineus* (Brown et al, "Detection of *Ehrlichia platys* in dogs in Australia", Australian Veterinary Journal, Vol 79, No 8, August 2001, pages 554-558). The organism is very difficult to detect (almost impossible by stained blood smear, because the platelets are so small) by any means other than Polymerase Chain Reaction, which actually detects its DNA. However, a quick screening method, for potential donor dogs, would be to perform a complete blood count (CBC). Any evidence of reduced numbers of platelets would rule that dog out as a plasma donor.

Any case of anaemia in a plasma donor would also be treated with strong suspicion for *E. platys* infection, as would any case of epistaxis (nose bleed)—a common sign of such infections, due to the Thrombocytopenia.

An easy method to diagnose this infection is to perform a platelet count on the blood of the animal in question, or by examination of the buffy layer in a spun microhaematocrit capillary tube. Deficiency of platelets (thrombocytopenia) is readily illustrated by either of these examinations.

In light of the above, preferably potential plasma donors will be subjected to a CBC, along with the above listed tests (DEA1.1 by Rapid VetH test and Indirect Coomb's Test) before donation. The abovementioned pathogens are merely common dog pathogens that a dog may encounter, especially in Australia, and it is appreciated that other pathogens may be considered. For example, pathogens that may be "endmic" to an area where the donor and/or recipient canines reside.

Vaccinations (Immunization and Hyperimmunization)

A feature of the invention is administration of antigens and other actives in a pharmaceutical composition to an animal, such as a canine. The actives may be "immunogenic agents", which are capable of eliciting an immune response in the canine. An immunogenic agent may comprise a vaccine or antigen presenting cell loaded or pulsed with an antigen. An immunogenic agent when administered to the canine is capable of eliciting an immune response against the immunogenic agent. A pharmaceutical composition includes an immuno-therapeutic composition. An immuno-therapeutic composition includes a vaccine. The immunogenic agent need not provide protective immunity to the host from a pathogen, and induction of the immune response in one aspect is sufficient. For example, production of an antibody capable of binding to the pathogen or part thereof may be sufficient to increase the concentration of antibodies in the isolated canine animal serum. Such an increase may be sufficient to improve the health of a canine.

Suitably, the pharmaceutical composition comprises a pharmaceutically-acceptable carrier. By "pharmaceutically-acceptable carrier, diluent or excipient" is meant a solid or liquid filler, diluent or encapsulating substance that may be safely used in systemic administration. Depending upon the particular route of administration, a variety of carriers, well known in the art may be used. These carriers may be selected from a group including sugars, starches, cellulose and its derivatives, malt, gelatine, talc, calcium sulfate, vegetable oils, synthetic oils, polyols, alginic acid, phosphate buffered solutions, emulsifiers, isotonic saline, and pyrogen-free water.

Any suitable route of administration may be employed for providing the animal with the pharmaceutical composition. For example, oral, rectal, parenteral, sublingual, buccal, intravenous, intra-articular, intramuscular, intra-dermal, subcutaneous, inhalational, intraocular, intraperitoneal, intracerebroventricular, transdermal and the like may be employed. Intra-muscular and subcutaneous injection is appropriate for administration of immunogenic agents described herein.

The immunogenic agents may be expressed by attenuated viral hosts. By "attenuated viral hosts" is meant viral vectors that are either naturally, or have been rendered, substantially avirulent. A virus may be rendered substantially avirulent by any suitable physical (e.g., heat treatment) or chemical means (e.g., formaldehyde treatment). By "substantially avirulent" is meant a virus whose infectivity has been destroyed. Ideally, the infectivity of the virus is destroyed without affecting the polypeptides that carry the immunogenicity of the virus. From the foregoing, it will be appreciated that attenuated viral hosts may comprise live viruses or inactivated viruses. Live vaccines are particularly advantageous because they lead to a prolonged stimulus that can confer substantially long-lasting immunity. Multivalent vaccines can be prepared from one or more different epitopes of one or more immunogenic agents.

A vaccine also comprises "naked DNA" vaccine as is known in the art, for example described in Barry, M. et al., (1995, Nature, 377:632-635) which is hereby incorporated herein by reference.

Preferably, a canine is immunized or hyperimmunized using the commercially available vaccines. Using such vaccines has been shown to typically result in the collection of plasma characterized by a uniform and high concentration of antibodies capable of binding to an antigen of the vaccine. It will be appreciated that the canine may be administered with a pharmaceutical composition comprising any suitable immunogenic agent and is not limited to those exemplified herein.

Vaccines for Canine Distemper, Canine Hepatitis, Parvovirus, Kennel Cough due to both Parainfluenza and *Bordetella bronchiseptica* are some suitable vaccines used in hyperimmunization. It is appreciated that other suitable antigens and vaccines may be selected by a person skilled in the art.

The vaccine is administered initially twice on a monthly basis, followed by half doses after each blood or plasma collection. This results in an immunity to these diseases that is higher than that in normal dogs receiving vaccinations only annually. It will be appreciated that although the donor may be immune to a disease caused by a pathogen, the term immunization comprises an induced immune response, both protective and non-protective.

A preparation of a registered vaccine is "Canine 4 Vaccine" (produced by CSL—comprising living attenuated distemper virus, living attenuated canine adenovirus type 2 (CAV2), living attenuated canine parvovirus type 2 (CPV2) and living attenuated canine parainfluenza virus), combined with "Canvac BB Vaccine" (produced by CSL—consisting of an inactivated cell free extract of *Bordetella bronchiseptica*, in an aluminium salt and 10% thiomersal). These vaccines may be administered in a same syringe.

In addition, to the above vaccines, an anti-endotoxin vaccine may be administered to the plasma donor canine animal. A preferred method for producing the vaccine is outlined in the Examples herein in relation to preparation of heat killed (inactivated) *E. coli* J5. This vaccine is produced primarily for prevention of Gangrenous Coliform Mastitis in dairy cows, see for example, Dosogne et al, 2002, Vet Res 33 1. The inventor has discovered that anti-endoxin vaccine is useful as an antigen in canine immunization/hyperimmisation for production of hyperimmune plasma for treating some conditions of a canine.

A building block, e.g. lipopolysaccharide (LPS, in particular LPS produced by *E. coli* J5), on which all other endotoxins are built, is a main component of the Anti-Endotoxin, or J5, vaccine. In the embodiment described herein, whole heat killed *E. coli* J5 is a component of an anti-endotoxin vaccine and accordingly a component other than LPS of *E. coli* J5 may be useful in inducing an immune response in a host. The vaccine is available in two forms, one combined with (Incomplete) Freund's Adjuvant, which considerably enhances the "antigenicity" of the vaccine, and a second, without any Freund's Adjuvant. Preferably, the vaccine does not comprise Freund's Adjuvant.

It will be appreciated that a vaccine may comprise one or more immunogenic agents from any suitable pathogen, such a virus, parasite and/or bacteria. A parasite may include for example an internal parasite such as heart worm and protozoal infections. It is also appreciated that whole intact pathogen, extract from whole pathogen and/or parts thereof may be used as antigens. Parts of the pathogen comprises: membranes, proteins, nucleic acids, LPS, polysaccharides and the like.

Hyperimmune and immune canine animal plasma in one embodiment comprises at least one immunoglobulin capable of binding to a component of a gram-negative bacteria. Preferably, the immunoglobulin is capable of binding a common gram-negative bacteria antigen. Preferably, the immunoglobulin is capable of binding an *E. coli* antigen. More preferably, the *E. coli* antigen is an *E. coli* J5 antigen. Not being bound by theory, *E. coli* J5 is thought to comprises a common antigen shared by gram-negative bacteria, e.g. *Salmonella, E. coli, Serratia* and *Pseudomonas*. Accordingly, use of *E. coli* J5 as an antigen results in production of host immunoglobulins capable of binding to gram-negative bacteria. The *E. coli* component is preferably a lipopolysaccharide, oligosaccharide or component thereof. The lipopolysaccharide in one embodiment preferably lacks an O-specific chain.

In another embodiment, the immunoglobulin is capable of binding to at least a part of other pathogens such as a virus or parasite as described herein.

Immunoglobulin comprises: IgM, IgD, IgG, IgA and IgE. The immunoglobulin is preferably produced by the donor dog, however, the immunoglobulin in one embodiment may be added to the isolated plasma before transfusion. Adding isolated immunoglobulins or antibodies to the isolated canine animal plasma may increase the concentration of an antibody to a specific pathogen, which may improve treatment of an animal. Immunoglobulins added to the plasma may be from the donor dog or other animal and/or isolated from cell culture. The immunoglobulin may be polyclonal or monoclonal. The invention also includes within its scope antibodies that comprise Fc or Fab fragments of the polyclonal or monoclonal antibodies. Antibodies may be purified from a suitable biological fluid of the animal by ammonium sulfate fractionation, affinity purification and/or by other methods well known in the art. Exemplary protocols for antibody purification are given in Sections 10.11 and 11.13 of Ausubel et al., supra, which are herein incorporated by reference. Immunoreactivity of the antibody against the native or parent polypeptide may be determined by any suitable procedure such as, for example, Western blot, ELISA and the like.

The isolated canine plasma may be supplemented with immunoglobulins as described above or other actives, for example pharmaceutical compositions including proteins, cytokines, carbohydrates and the like. A supplement may be selected in part on a condition of the recipient, for example to assist with recovery and/or treatment of an ill recipient.

There are no bovine by-products used in the production of the preferred vaccines, especially from the UK and EC, nor are any genetically modified products.

Plasma Collection (Plasmapheresis or Apheresis)

Plasmapheresis, or Apheresis, is a process whereby a donor's own blood is removed, particular fluid and cellular elements are collected from the blood and the non-collected blood component(s) returned to the same donor.

Plasma is collected with the canine donors under general anaesthesia, or at least heavy sedation/narcosis (described herein), with replacement intravenous fluids administered simultaneously, during the course of the collection. If anaesthesia is used, the anaesthetic is preferably a mixture of ultra short action intravenous agents ("Diprivan", 10 mg/mL Propofol, manufactured by Astrazenica) for induction, and maintenance on a mixture of Halothane and oxygen, administered via an intratracheal tube, by a Stevens anaesthetic machine.

Anaesthesia is monitored using an amplified oesophageal stethoscope, under the supervision of a veterinarian throughout.

The present invention significantly improves the quality of canine plasma. Administration of plasma produced in accordance with the present invention may improve treatment of many medical conditions in the canine, in terms of survival rates and reduction in cost of treatment, and shortened periods of hospitalization.

An average plasma volume collected is about 1,200 mL (6×200 mL bags) is typically collect per 35 Kg dog.

Due to a smaller body mass of a dog compared with a human or horse, supplemental (intravenous) fluids are preferably administered. A sterile, isotonic, saline solution is administered intravenously at three times maintenance rate (10 mL/Kg body weight/hour=400 mL/hour for 40 Kg dog), for the duration of the plasma collection process.

Two lines are inserted into veins of the donor canine, one line collects blood by the plasmapheresis machine (usually in the Jugular Vein in the neck) and the other line is for the provision of fluid replacement (usually in the Cephalic Vein in one of the front legs). Movement by the donor has the potential to interfere with the collection considerably by disruption to these catheters from the veins.

Pre-Collection Steps

The donors are fasted for at least 8 hours before anaesthesia.

A pre-medication or pre-general anaesthesia injection comprising a combination of Acetylpromazine 2 mg/mL (dose rate of 0.2 mg/Kg body weight) and Atropine Sulphate 0.6 mg/mL (dose rate of 0.05 mg/Kg body weight) is administered subcutaneously, preferably in a same syringe. The injection and the doses used are recorded in the Anaesthetic Log.

The plasmapheresis machine is powered on, a sterile, single-use collection kit installed, and the machine "primed" and made ready for use. The first bag is connected to the collection kit.

After administration of the pre-medication injection, general anaesthesia is induced by administration of an intravenous injection of Propofol 10 mg/mL at a dose rate of 2-4 mg/Kg body weight, or an ultra short-action barbiturate ("Pentothal Injection, Abbott Laboratories, Thiopental sodium 50 mg/mL at a dose rate of 10-20 mg/Kg body weight) to a surgical depth/effect considered necessary by the anaesthetist. The donor is placed in lateral recumbency (lying on its side).

A cuffed intratracheal tube is inserted into the trachea, the cuff suitably inflated, and the tube connected to a closed-circuit Stevens Anaesthetic Machine fitted with a vaporizer primed with "Halothane" and soda lime canisters, and oxygen Oxygen and Halothane are administered to the canine at an amount considered appropriate by the anaesthetist (usually 2% Minimum Alveolar Concentration; MAC) for maintenance of anaesthesia.

A monitoring device, such as an amplified oesophageal stethoscope is inserted into the oesophagus, to the level of the heart, for monitoring heart sounds and rate and respiratory sounds and rate. Alternatively, an Apnoea Alert may also be used.

Sterile isotonic saline is administered via a catheter inserted into the cephalic vein of the uppermost foreleg at a rate considered appropriate by the anaesthetist (approximately three times maintenance level or 10 mL/Kg/minute, 400 mL/minute for 40 Kg dog). These fluids are administered throughout the duration of the collection procedure.

A second catheter is inserted into the uppermost jugular vein and inserted retrograde (pointing towards the heart) into the vein for collection of blood.

Collection Steps

The following is a general method for plasma collection and collection parameters are shown in Table 2.

1. A collection it as described in FIG. 1 is fitted to a Haemonetics PCS Plus plasma collection machine that has been sterilized with ethylene dioxide gas. The machine is powered "on", and the parameters checked as the PCS is booting up. Care is taken to minimize contamination of the Transfer Bag spikes and the Anticoagulant Bag spikes during connection to the sterile Collection Kit. Bowl Optics and Line Sensors are checked, and, if necessary, wiped clean using paper towel moistened with methylated spirits.

2. Anticoagulant (4% trisodium citrate) is connected to the appropriate line(s) and the machine is "primed" with anticoagulant. Other anticoagulants may be used, including for example 5% acid citrate dextrose.

3. An intravenous fluid bag (one liter 0.9% sterile saline) is spiked with a commercially available fluid administration set and mounted on the transfusion stand.

4. The donor dog for plasmapheresis, fasted for 8 hours before anaesthesia and has not had plasma collected for at least three weeks prior to the present collection, is installed into a recovery cage located in a collection suite, and is sedated. Typical sedation for a standard 32 Kg greyhound donor is simultaneous subcutaneous injection of 1.2 mg Acetylpromazine Maleate and 0.3 mg Atropine Sulphate, mixed into the same syringe. A period of at least 20 minutes, and no more than 30 minutes, is allowed to pass before an anaesthetic agent is administered.

5. A venipuncture site in the Cephalic Vein is clipped and swabbed with an antiseptic solution.

6. An anaesthetic induction agent is administered for general anesthesia approximately 140 mg Propofol is administered as an intravenous bolus, via the Cephalic Vein. Propofol 10 mg/mL at a dose rate of 2-4 mg/Kg body weight, or an ultra short-action barbiturate ("pentothal injection; Abbott Laboratories, Thiopental sodium 50 mg/mL at a dose rate of 10-20 mg/Kg body weight) to a surgical depth/effect considered necessary by the anaesthetist. The donor is placed in lateral recumbency (lying on its side). A "surgical" level of anaesthesia is induced by this treatment.

7. When asleep the dog is placed in lateral recumbancy, and the collar (on which is the dog's name and donor number) is removed.

8. An 8.5-9.5 mm cuffed intra-tracheal tube is inserted into the dog's trachea, and the cuff inflated with about 20 mL of air. The tube is connected to the Stephens type gaseous anaesthetic machine, with oxygen supply and Halothane vaporizer, filled with Halothane. The vaporizer is continually adjusted to a level commensurate with the achievement of plane III general anaesthesia, usually 2% Minimum Alveolar Concentration (MAC).

9. An apnoea alert monitor is connected into a Y adaptor at the tracheal tube adaptor and is switched on, with the apnoea interval set at 20 seconds, and the sensitivity set at 5. Another monitoring device, such as an amplified oesophageal stethoscope may also be utilized, and is inserted into the oesophagus, to the level of the heart, for the monitoring of heart and respiratory sounds and rate.

10. An intravenous catheter (usually 20 gauge 1.5 inch) is inserted into the same Cephalic Vein as above and an isotonic saline infusion started, at a rate of approximately 20 mL per minute. The saline infusion is continued for the duration of the collection to minimize the effects of dehydration on the donor. If "flow" problems are encountered, the rate of fluid administration is increased. If these problems continue, the Technician digitally occludes the Jugular Vein at the base of the neck.

11. The plasma collection site over the uppermost Jugular Vein is then clipped and surgically prepared using alternate applications, via spray bottles of methylated spirits and 2.5% Povidone-Iodine, repeated five times.

12. The Jugular Vein is then catheterized (retrograde) with a 14 g, 2" intravenous catheter, and the plasma collection line connected, and the PCS machine started on DRAW.

13. The collection line and catheter is bandaged to the donor dog's neck with an elastic adhesive bandage, to prevent the catheter slipping out of the vein, should the plane of anaesthesia become too light, and the dog starts to struggle.

14. Once the PCS commences to DRAW, the pump is immediately manually set at a maximum collection speed of 85 mL/minute, or that which the technician deems appropriate, thus starting the pheresis process. During "Draw", as the plasma level rises to the top of the centrifuge bowl, and plasma begins to issue from there, 20-30 mL plasma, constituting sample 1, is collected into the sample bag attached to the second fork of the "Y" connector, which is installed with the disposable collection kit. After this sample is collected, the sample line is clamped and the collection line is unclamped (simultaneously) and the collection proceeds.

15. While plasma is being drawn, it is being collected into a "reservoir" bag of 2 liters capacity, and this bag is permanently placed on the electronic scales. Alternatively, use of a split-fill method may be used as described in Example 5.

16. The "Draw" cycle is completed when a Plasma Line Cell Monitor (PLCM) detects platelets (the lightest of the blood cells and therefore the first to appear here) and/or other blood cells in the line. Sometimes, this will be seen as a "cloudiness" of the plasma in the line by the operator, and the process of closing the PLCM can be performed manually by the operator, terminating that "Draw" cycle.

17. Upon completion of the "Draw" cycle, the machine automatically starts to "Return" the remaining red cells to the donor dog, the pump speed is manually selected at 75 mL per minute, or that deemed appropriate by the technician.

18. During the "Return" cycle TP measurements are made, lines clamped, results recorded, and urine and faeces passed by the donor manually removed, as this cycle requires much less close supervision of the PCS than the "Draw" cycle.

19. During the first "draw" and "return" cycle, the first sample is collected. This sample is used for measurement and determination of blood cell contamination of that batch of plasma. The test is usually performed by an independent laboratory with appropriate accreditation.

20. One more retention sample is collected at the completion of the collection, from the reservoir bag. This final sample is used for sterility testing and gamma globulin determination. This bag is used for these tests because contamination by micro-organisms is likely to be greatest and gamma globulin (GG) concentration is most likely constant, given that all of the plasma collected is mixed in the reservoir bag.

21. After the final "draw" and "return" cycle the blood cells are returned to the donor and the collection harness emptied, the collection statistics have been recorded from the console onto the Daily Chart, the PCS is powered "OFF" and the harness and catheter removed from the donor Jugular Vein. The technician immediately applies digital pressure, using a betadine swab, to the venipuncture site to prevent formation of a haematoma. If necessary, a thick swab is placed under the dog's collar, once it is re-applied, for longer term pressure to the puncture site.

22. The anaesthetic machine Halothane vaporizer is switched OFF during the final cycle, to facilitate as rapid a recovery from anaesthesia as possible.

23. The cuff on the intratracheal tube is deflated, to allow the donor to breathe some atmospheric air.

24. Once the donor begins to regain consciousness, the saline line is also removed from the Cephalic Vein, if used, and digital pressure applied.

25. The intratracheal tube is removed from the dog's airway, often when the dog starts chewing on the tube.

26. A maximum amount of plasma to be collected is set at 1,740 mL for a standard 32 Kg greyhound donor, unless previous experience with this particular donor indicates otherwise. This will fill 8×200 mL transfer bags and an extra 140 mL is consumed in plasma line wastage and the collection of retention and quality control samples. This figure has been arrived at by experience, as this is the maximum amount which can be collected, still allowing us to achieve our twin aims of maximizing the amount collected which meets our specifications, and having no adverse impact on the donor animal. This 1.74 L plasma is collected into a standard 2 L transfer bag.

27. After the collection is completed, the 200 mL bags are then gravity filled from the reservoir bag, to a weight of 204 g (after the bag has been 'tared' on the scales). The weight of 204 g plasma is equivalent to the required volume of 200 mL.

The above method minimizes contamination of the isolated plasma by blood cells. A preferred maximum levels of blood cells are: red cells—30,000 million/L of plasma, white cells—200 million/L of plasma and platelets—50,000 million/L of plasma. As the indicated levels are preferred maximum levels, plasma comprising even less cells and platelets is more preferred, for example: (1) red cells at a plasma concentration of 25,000 million/L, 20,000 million/L, 10,000 million/L and even 2,000 million/L and less; (2) white cells at a plasma concentration of 175 million/L, 150 million/L, even 100 million/L and even 1 million/L and less; and (3) platelets at a plasma concentration of 45,000 million/L, 40,000 million/L, 30,000 million/L and even 8,000 million/L and less. Most preferably, the plasma does not comprise detectable levels of red cells, white cells and/or platelets. Other levels may be acceptable, but less preferred, for example: (a) red cells at a plasma concentration of 35,000 million/L, 40,000 million/L and 50,000 million/L; (b) white cells at a plasma concentration of 215 million/L, 225 million/L and 250 million/L; and (c) platelets at a plasma concentration of 55,000 million/L, 60,000 million/L and 75 million/L.

The top portion of the centrifuge bowl comprising less than about 50% of the total volume of the centrifuge bowl, more preferably less than about 25%, even more preferably less than about 20%, still more preferably less than 10%, less than 5% or even less than 1% of the total volume of the centrifuge bowl.

Preferably, the centrifuge bowl is rotated at a speed between 4,500 rpm-6,000 rpm.

Preferably, the total plasma protein concentration of the isolated plasma is at least about 25 g/L, 30 g/L, 35 g/L, 40 g/L 45 g/L and 55 g/L or more. Although a higher plasma protein concentration is preferred, the isolated plasma broadly covers isolated plasma having a total plasma concentration less than 25 g/L, for example, less than 20 g/L, 15 g/L, 10 g/L, 5 g/L, 4 g/L and even less than 2 g/L.

Preferably, the gamma globulin plasma concentration of the isolated plasma is at least about 6 g/L, 8 g/L, 10 g/L, even more preferably at least 12 g/L, 15 g/L and most preferably at least 18 g/L, 20 g/L and 21 g/L.

It will be appreciated that although the preferred cell separator is a centrifuge because of ease of use, efficiency and minimal time required to separate plasma from cells, other cell separators may be used. For example, filters and membranes that are known in the art may be used, including commercially available filters. Such examples include MultiScreen Ultracel-PPB membranes/filters available from Millipore and PES and PVP blended membranes available from Spectral Diagnostics, Inc, USA.

Post-Plasma Collection

After the plasma collection is completed, the jugular catheter is removed, administration of halothane and oxygen is terminated, tracheal tube is removed and administration of intravenous fluid continues until the canine animal is removed from the collection table.

Collection of plasma in accordance with a preferred form of the invention comprises the following advantages:—
1. It is a completely closed system, using a sterile, single-use and disposable collection kit, therefore the plasma is sterile and non pyrogenic, which is safer for recipient and donor.
2. The donor loses little or no red blood cells. This means that collections can proceed as often as three-weeks without concern of anaemia developing in the donor.
3. The process involves so little physiological stress and accordingly is sufficiently gentle, that the donor suffers no untoward side-effects or physical stress of any nature from donating plasma.

Plasmapheresis is a harmless, well tolerated procedure, which collects large quantities of high quality plasma at more frequent and regular intervals than other techniques.

The plasmapheresis machine used in accordance with the preferred embodiment of the invention is a modified form of a machine used in human blood banks (e.g. software and hardware have been modified).

One problem with applying human blood collection procedures to animal donors is that it is not possible to explain to the animal what is occurring and therefore one cannot expect or guarantee total co-operation from the donors. Accordingly, a method of restraint is used, usually in the form of sedation, narcosis, or general anaesthesia.

The preferred method of the present invention includes the following steps:
Collected plasma is tested for sterility.
Plasma is collected from dogs of known blood type to qualify as Universal Plasma Donors.
Collected plasma is tested for potency (eg. gamma globulin concentration).
Dogs are contained in a closed quarantined group to minimize risk of donors incubating an infectious disease at the time of collection, which may result in the collection of plasma which contains viruses.

Plasma is preferably hyperimmune plasma, which has advantages over normal non-hyperimmune plasma. Hyperimmune plasma is more potent not only in antibody concentration, but also all other substances normally contained in the plasma, e.g. clotting factors, fibrinogen, opsonins, interferons. Higher potency may also refer to a greater biological activity.

Canine animal plasma made in accordance to the present invention results in improvements in treatment of medical conditions in terms of survival rates and reduction in cost because of shortened periods of hospitalization.

Some medical conditions and situations that may benefit from the intravenous administration of plasma made in accordance with the present invention include:—

Parvovirus infection—where there is severe intractable diarrhoea, with accompanying dehydration, protein loss, infection and endotoxaemia (release of very harmful bacterial poisons into the circulation, which cannot be combated by antibiotics or any other agent, except plasma which is rich in anti-endotoxic antibodies).

Pancreatitis—inflammation of the pancreas, which causes over-production of pancreatic protease enzymes, amylase and lipase. These enzymes, when secreted by the pancreas (in normal situations triggered by eating a normal meal), pass via the pancreatic duct into the intestine, aiding digestion. When over-produced (such as by eating large, fatty feeds, or rotten, decaying food), the enzymes can be secreted to excess and subsequently "overflow" into the blood stream, causing very severe emergency medical problems, such as Endotoxaemia, infection and coagulopathies.

Interference with blood coagulation—such as with:—
poisoning by the various rat poisons—plasma comprises all of the clotting factors (intact) that are present in normal whole blood
snake envenomations (bites)
advanced blood loss, resulting in depletion of clotting factors from the blood stream, resulting in a condition known as disseminated intravascular coagulation (usually rapidly fatal)
Congenital Haemophilia, such as in Doberman's with Von Willebrand's Disease
pancreatitis Severe infection characterized by high blood concentrations of bacteria, bacterial fragments, and/or endotoxins.

Prolonged major surgery.

Massive tissue injury and destruction such that from a car accident, or crushing injuries.

Pyometron (where the uterus fills with pus)

Prostatic abscessation

Most typical treatments involve long and costly courses of intensive care with low chances of a successful outcome. However, all the abovementioned conditions have been successfully treated using plasma made in accordance with the present invention with outstanding results.

In addition to the above conditions, other conditions may be determined by a person skilled in the art that are suitable for plasma therapy. Diseases may be treated and/or symptoms improved by administering hyperimmune plasma made by administering a donor canine animal with an antigen(s) associated with a particular disease. For example endotoxin and/or viruses as described herein.

In order that the invention may be readily understood and put into practical effect, particular preferred embodiments will now be described by way of the following non-limiting examples.

Example 1

Testing Prospective Donor Dogs as Suitable for Donating Plasma

Dog Erythrocyte Antigens (DEA)

A donor dog is preferably characterized by a blood group whose plasma will not cause a plasma transfusion reaction nor trigger haemolysis (e.g. universal plasma donor). Preferably, the canine is negative for at least one Dog Erythrocyte Antigen (DEA). The at least one DEA is preferably selected from the group consisting of: DEA1.1, DEA1.2, DEA3, DEA5, DEA6, DEA7 and DEA8. The canine is preferably at least negative for DEA1.1. More preferably, the canine is farther negative for DEA1.2 and/or DEA7. DEA1.1 may be detected using commercially available kits, including Rapid Vet H card test (Jain N C, Schalm's Veterinary Haematology, 4$^{th}$ Ed. 1986, pp 73-75).

A suitable canine for use as a plasma donor is the greyhound, which comprises a low frequency of DEA1.1, DEA1.2 and DEA7 blood group antigens.

Although blood typing of a donor dog is sometime performed in relation to whole blood transfusions and transfer of packed blood cells to a recipient, the present invention in one aspect includes the step of blood typing a donor dog for a plasma transfusion.

Anti-Globulin Antibodies

The canine is also preferably negative for anti-globulin antibodies. Presence of anti-globulin antibodies may be determined using a Coombs test (Jain, 1986, Schalm's Veterinary Haematology, 4$^{th}$ Ed, pp 73-75), incorporated herein by reference. There are two types of Coomb's Test: (1) a Direct Coomb's Test is used to detect anti-globulin antibodies on the surface of the patient's (in this case, the prospective plasma donor's) red cells and (2) an Indirect Coomb's Test is used to detect anti-globulin antibodies in the patient's (prospective donor's) plasma or serum, or eluates from the red cells. According to Jain et al, 2000, Veterinary Hematology, 5$^{th}$ Ed, p 804, the Indirect Coomb's test is not valid for use in veterinary species, because of the low incidence of non-cell-bound autoantibody (ie free autoantibody in the plasma). However, if small numbers of red cells were to be suspended in the plasma, the possibility for adverse reactions to transfusion of that plasma exists. The inventor has experimentally demonstrated that a significant number of red cells may be present in plasma before the plasma takes on a "pinkish" coloration, which is well above a suitable preferred limit.

Preferably, the canine is negative for both DEA1.1 and anti-globulin antibodies. More preferably, the canine is further negative for DEA1.2 and DEA7. Accordingly, a donor's blood will not comprise any naturally occurring antibodies to blood groups other than its own. The donor is also preferably free of known blood borne diseases. The donors are quarantined at all times to minimize risk of incubating infectious diseases. Preferably the donor will not have ever received a transfusion of blood or any blood product previously in its life, or, if female, never have given birth—either of these scenarios may possibly lead to the production of antibodies to other blood groups.

Viruses and Blood-Borne Agents

Donor canines are preferably hyperimmunized with commercially available vaccine(s) prior to plasma collection. Accordingly, it is argued that there is little or no need for viral screening of potential donor canines prior to plasma collection.

Performing a complete blood count (CBC) on potential donor canines to determine a reduced numbers of platelets will screen for a potential infection by *Ehrlichia platys*. Accordingly, a donor canine comprising a low platelet count will be excluded from plasma donation. *Babesia canis* infection is not considered to be a high priority test for screening potential plasma donors because of the nature of this infection (parasite of the red cells) and the infection is localized to Northern Queensland.

Plasma will be collected at minimum intervals of 3 weeks, only from dogs in good health and of suitable body condition, weight and age. A donor dog is preferably more than 12 months of age, 35 Kg body weight, desexed, and all husbandry and hyperimmunization vaccination procedures described herein completed.

Example 2

Hyperimmunization Schedule for Donor Dogs

Vaccinations for Canine Distemper, Canine Hepatitis, Parvovirus, Kennel Cough due to both Parainfluenza and *Bordetella bronchiseptica* are commercially available. Vaccines used for hyperimmunisation include: "Canine 4 Vaccine", (produced by CSL—consisting of living attenuated distemper virus, living attenuated canine adenovirus type 2 (CAV2), living attenuated canine parvovirus type 2 (CPV2) and living attenuated canine parainfluenza virus "Canvac BB Vaccine" (produced by CSL—consisting of an inactivated cell free extract of *Bordetella bronchiseptica*, in an aluminium salt and 10% thiomersal).

An anti-endotoxin vaccine (*E. coli* J5 Vaccine) is preferably prepared according to the method below. However, it will be appreciated that other forms of an anti-endotoxin vaccine may be prepared as is known in the art and/or which may be prepared by a person skilled in the art.

1. Plate out of *E. coli* J5 from freeze dried culture onto 5% Sheep Blood Agar (SBA) and MacConkey Agar (MAC). Incubate at 37° C. for 24 hours.

2. If necessary, restreak from original SBA plate until sure growth of *E coli* obtained. Incubate 2-3 colonies into 100 ml of Tryptone Soy Broth (TSB). Need 100 ml of seeded TSB per large plate of Sensitivity Agar. Also inoculate pure culture into Cooked Meat Broth and onto fresh SBA plate for future freeze drying.

3. Incubate TSB at 37° C. overnight, on roller or shaker. Flood 100 ml seeded TSB onto stainless steel tray (27×22 cm) containing 400 ml prepared and sterilised Sensitivity Agar. Keep lids closed and wrap tray in alfoil to maintain moisture. Incubate 37° C. overnight. (Be careful with this step—trays easily contaminated!)

4. Harvest culture into 200 ml PBS/tray of agar to a level of approx 10$^9$ bacteria/ml. (MacFarland Standard Autoclave PBS 15 lb/15 minutes. Cool on bench overnight).

5. Next day perform Sterility Testing. 0.5 ml of autoclaved PBX inoculated into Cooked Meat Broth. Incubate 37° C./24 hours.

6. From Cooked Meat subculture onto SBA (aerobic and anaerobic) and MAC 37° C./48 hours. If sterility check fails add Formalin to each failed bottle of PBS to a concentration of 0.5%, then repeat Sterility Tests.

7. Dispense vaccine into:

(a) 5 ml into 0.5 oz bottle—labelled "E. coli J5 (heat killed)"

(b) E. coli J5 adjuvant—mix 5 ml E. coli J5 heat killed vaccine in equal amounts of Freund's incomplete adjuvant.

Both vaccines are to be stored frozen at −4° C.

A small dose is initially administered (1 mL by intramuscular injection into the pectoral muscles) without Freund's Adjuvant, followed by two doses of mL each (subcutaneously) of the J5 vaccine without Freund's Adjuvant. Further immunization (hyperimmunization) is performed, with a half-dose (0.5 mL) subcutaneously after every plasma collection. Table 1 shown a typical hyperimmunisation schedule.

Example 3

General Plasma Collection Protocol

Plasmapheresis or Apheresis

FIG. 1 is a diagram showing a preferred form of the plasma collection apparatus, comprising a collection kit. The collection kit comprises components made of disposable polypropylene, which improves ease of use and sterility when isolating plasma. The collection kit comprises items 20, 21, 23, 30, 34, 40 and 100 as shown in FIG. 1 and described hereinafter. The collection kit for a plasmaphoresis machine (HAEMONETICS PCS PLUS, Haemonetics Corp) is sterilised using ethylene dioxide gas. The collection kit is fitted to the machine, all tubes and a Centrifuge Bowl or rotor 100 primed (treated) with anticoagulant 4% trisodium citrate. A catheter (blood line 30) inserted into the jugular vein of a donor canine 11 is connected to the HAEMONETICS PCS PLUS via blood line 30 and collection kit and the plasmapheresis process initiated.

As shown in FIG. 1, bag 20 (500 mL comprising an anticoagulant (4% trisodium citrate) is attached to anticoagulant pump 22 via line 21. The anticoagulant is mixed with the blood issuing from the canine donor 11 via anticoagulant line 23 that connects to Y-connector 24. Blood mixed with anticoagulant travels via blood line 30 through one or more blood line air detectors (BLAD) 31 for detecting air in the lines. Blood pump 32 pumps blood from the canine 11 to a centrifuge 60 via line 34. A donor line air detector (DLAD) 33 is located on line 34 to detect air in the line. Blood is pumped into a centrifuge bowl 100 located inside the centrifuge well 60 with a freely rotatible base to which the centrifuge bowl 100 is attached and the blood is separated into an isolated plasma component and an isolated blood cell component by rotating the centrifuge bowl 100, shown in more detail in FIG. 2. Plasma exits the centrifuge bowl 100 via a plasma line 40. A plasma line cell monitor (PLCM) 41 is located on the plasma line 40 to detect blood cells. In one embodiment, the PLCM 41 is bypassed by plasma line 40. The plasma line 40 splits into a plasma collection line 42 and a discard or dump line 50. A valve (dump line valve) 51 is located on the discard line 50 to regulate flow to dump bag 52. Fluid collected in dump bag 52 is typically discarded, but the contents may be examined to assess the concentration of: blood cells, total protein, gamma globulin, antibodies, etc. The plasma collection line 42 comprises a plasma valve 43 that is capable of regulating fluid flow to plasma collection bags 44 and 45. Plasma collection bag 44 is shown located on a scale 46 that measures the weight of the collected plasma. It will be appreciated that one or more plasma collection bag(s) may be used, for example as shown by plasma collection bags 44, 45. Accordingly, the actual number of bags may be any suitable number. When a single plasma collection bag is used, the total protein concentration of plasma from a donor is uniform in the single reservoir bag. Alternatively, as described herein a "split fill" method may be used when a plurality of plasma collection bags are used.

Figure 2:
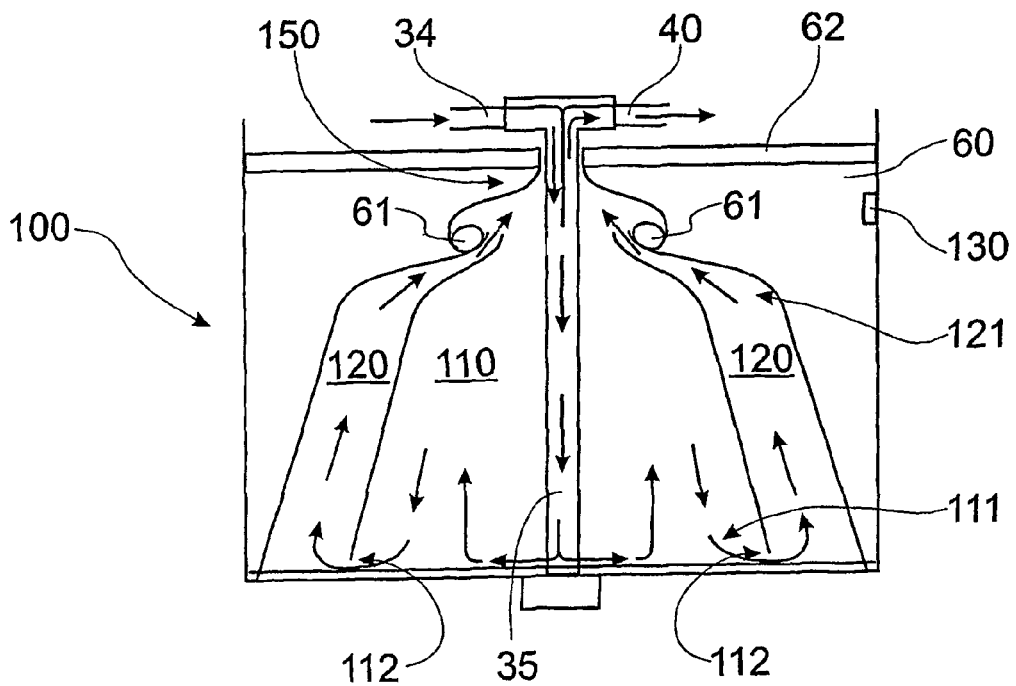
FIG. 2 is a side cross section of a centrifuge bowl.

A schematic of the centrifuge bowl 100 is shown in FIG. 2. Blood enters the centrifuge bowl 100 via the blood line 34 and isolated plasma exits the centrifuge bowl via plasma line 40. Arrows indicate the direction of flow through the centrifuge bowl 100. The centrifuge bowl 100 comprises an inner bowl 110 in which blood initially enters via a centrally located tube 35. At a bottom 111 of the centrifuge bowl 100, contents the blood is directed to an outer bowl 120 through openings 112 while the centrifuge bowl 100 is rotating. Less dense material first moves into the outer bowl 120, for example plasma. As the components of the blood, e.g. blood cells and plasma, separate, the plasma rises towards an upper portion 121 of the outer bowl 120 and out of the centrifuge bowl 100 via plasma line 40. A spill detector 130 may be located within the centrifuge 60. A centrifuge bowl lid 62 is sealed to the centrifuge bowl 100 by O-rings 61. The section of the centrifuge bowl below location 150 rotates, while the section above is held firm by a centrifuge lid 62.

The centrifuge bowl 100 comprises a volume capacity of 200 mL and is placed within the centrifuge 60 of the plasmaphoresis machine. The centrifuge bowl 100 is rotated at 4,500 rpm-6,000 rpm, preferably in a range between 4,800 rpm-5,650 rpm (actual rpm may be manually adjusted during collection). During a plasma "draw" step, the centrifuge bowl 100 pools blood at bottom 111 and while the centrifuge is rotating the blood flows outward and upward in the outer bowl 120 separating the blood into components according to density. A less dense component comprising plasma separates to the upper portion 121 of the outer bowl 120, followed by platelets, buffy layer (comprising of white blood cells and platelets), and finally packed red cells. As the plasma fills the outer bowl 120, the plasma flows out of the outer bowl 120 and into a plasma line 40.

The plasma flows via the plasma line 40 to the dump bag 52 that collects air in the harness and a first flow of plasma, which ensures that the plasma is cell free. Plasma then flows into a sterile one liter plasma collection bag 44 and 45 (preferably a single use collection kit described above) until the plasma cell line monitor 41 (or a technician if 41 has been bypassed) detects a first sign of blood cells (platelets) passing therethrough, at which time both the plasma line valve 43 is closed and the dump line valve 51 is opened. At this point the centrifuge bowl 100 starts to brake (slow down), and any further plasma issuing from the outer bowl 120, between the application of the brake and the final stopping of the centrifuge, is collected into the dump bag 52.

When the centrifuge ceases to rotate, the plasma machine initiates a "return" step, whereby the remaining contents of the centrifuge bowl 100 (e.g. blood cells including packed red and white cells and platelets) are returned to the donor canine 11, thus preventing or minimizing development of acute anaemia.

Although the centrifuge bowl 100 comprises a volume of 200 mL, approximately 500 mL of blood will have been collected from the donor canine 11 in one cycle, at pump collection speeds of up to 80 mL/minute in one complete cycle, resulting in about 200 mL of plasma collected, which is variable, depending in part on a donor's haematocrit at the start of the collection. After the "return" step is completed, the plasma "draw" step automatically re-commences and the process is repeated.

The plasma collection bags 44, 45 (or "transfer bags") have a capacity of 300 mL and are supplied, sterilised by gamma irradiation, in outer bags. They have a single filling port with two spikes, connected by a Y-connector, which allows filling as described herein, and two transfusion ports, for administration to a patient via a blood giving set with a 20 micron filter.

When the transfer bag is attached to the HAEMONETICS PCS PLUS plasma line in such a way as to preserve sterility, using the first spike, the second spike is sealed temporarily by a disposable slide clamp. When the first bag has been half-filled with approximately 100 mL plasma (which is roughly one "draw" cycle in a donor with a normal haematocrit), that line on the transfer bag is then clamped with another slide clamp. In addition to using a series of multiple collection bags, a single reservoir bag may be used.

A standard collection from a canine donor is 6 bags of plasma, 200 ml per bag. An exact volume collected will depend in part on a weight of the dog, and its previous history of plasma donation. Plasma is collected at minimum intervals of 3 weeks, only from dogs in good health and of suitable body condition, weight and age.

The process oscillates between "draw" and "return" steps a plurality of times, until the collection has reached an end point (as determined by tests described herein). The plasmapheresis machine is switched off after completion of a final "return" step, the catheter removed from the donor and the soiled kit removed from the plasmapheresis machine and discarded.

Example 4

Gamma Globulin (GG) Assessment

During plasma collection, the gamma globulin (GG) concentration of the plasma collected decreases roughly in a linear manner. Because the volume collected from the dog is small, this means that the GG concentration falls more steeply from start to finish, than it falls in plasma collections from a larger animal. Accordingly, in one embodiment of the invention, this step of determining GG concentration of the collected plasma assures that a desired GG concentration is present in the isolated plasma. A suitable predetermined plasma GG concentration may be determined and plasma collection terminated when this predetermined GG concentration is determined in the collected plasma. Examples of some of the decrease in GG concentration during plasma collection in canine (where the "split-fill" method was not employed), are shown in Table 3. Data included in Table 3 is from dogs that were not hyperimmunized. This suggests that their GG concentration may have initially been lower than that of hyperimmunised dogs and also decreased more quickly during plasma collection. In addition, although thoroughly clinically examined before collection, some of these donors may not have been in the best of nutritional condition as they were Council dogs destined for euthanasia. This was carried out on the morning after the collection once it was observed that they recovered from the process without any untoward sequelae.

As shown in Table 3, the method of "Split-filling" of the plasma bags is important to maintain uniform gamma globulin concentration throughout the collection bags Sterile Transfer Bags of 350 mL capacity are used comprising two sterile spikes. The only bags commercially available smaller than 350 mL bags are 150 mL, which are too small for practical transfusing of dogs. In any case, 200 mL of plasma in a bag of 350 mL capacity is desirable, because the bag is under less pressure when filled, allowing greater insurance against breakage once frozen, and more flexibility in placing into its box before freezing. Also, smaller bags will not be big enough for an NRA registered label to adhere to completely, without overlapping at the edges.

A part of a line distal to a clamp is cut and the plasma in that section is measured for its plasma protein content immediately using a hand-held refractometer.

This gives a rough indication of GG concentration, such that a reading on the refractometer of 40 g/L plasma protein or above correlates with a GG concentration considered at least normal in the normal dog (5-18 g/L), see Ducan et al, "Veterinary Laboratory Medicine-Clinical Pathology" $3^{rd}$ Ed, pages 112 and 238). Alternatively, in donors immunologically stimulated by hyperimmunization as outlined herein, the reading would correlate with a GG concentration of 10-18 g/L, or above. The resultant plasma protein reading is noted on the label of the transfer bag, along with the date, the collection number, the donor dog's name and number, and the bag number. The half-filled bag is then placed in a polystyrene ice box on ice.

Alternatively, another method of collecting the plasma in such a way as to ensure that all bags of plasma are of uniform GG concentration is to collect the plasma in the first instance into a "reservoir" bag as described in Example 3 and decanting the plasma, once fully mixed, into final (treatment unit) bags after the collection is terminated.

Example 5

In-Process Control Tests

"Split Fill" Method of Bag Filling

A "split-fill" method of filling the collected plasma bags is used to yield bags of substantially uniform gamma globulin concentration.

The plasma collection bags are sequentially half filled (e.g. 100 mL for a total 200 mL volume) in a same manner until the total plasma protein reading falls to a level of 30 g/L, whereupon no new bags are used. At this point, all of the half-filled bags are then completely filled (e.g. to 200 mL), in reverse order, through a second sterile spike, to a weight of 234 g, according to scales built into the plasma collection machine. Because of the specific gravity of plasma, this weight (after some loss, which occurs in the act of expressing air bubbles from the bag, which invariably occur, because the plasma "froths" during collection, leaving the target 204 g) will most closely approximate 200 mL in volume.

No bag with a mixed plasma total protein of less than 25 g/L (and therefore a GG concentration of less than 10 g/L) is retained.

The second spike is then sealed with a slide clamp, the contents of the bag thoroughly mixed and any air bubbles that have collected in the transfer bag during filling are expressed, through a loosened slide clamp. This ensures that a non-stop, continuous flow of plasma and bubbles runs to the outside, so that no air and therefore possible contaminants are sucked into the transfer bag. The bag is then finally sealed with a stainless steel grommet, clamped into place as close as possible to the transfer bag itself, by pliers. The filling tube then removed contains a uniform sample of plasma, representative on the contents in the bag itself, and the plasma protein (PP) concentration as measured by the refractometer is then read and this final reading recorded on the bag label and in the Daily Chart. The PP level of the second spike tubing can also be measured before the mixed bag PP level, and the average of the readings from the first half-fill and the second half-fill will equate with the actual full mixed-bag PP reading, as demonstrated by the inventor in practice. Therefore, the reading of the PP level of the second spike tubing is not necessary, provided the mixed bag full-fill PP reading is always obtained, as is preferred.

From all of the above, it can be seen that the system, utilising properly sterilised components completely, is completely closed, negating or minimising possibility of contamination, accidental or otherwise, of collected plasma.

Characteristics of the Isolated Plasma

The plasma is a completely natural product and preferably no preservatives are added. As stated previously, a TGA approved anticoagulant (4% Trisodium Citrate sterile solution) is added, to act as an anticoagulant in the plasma collection process. Other known anticoagulants known in the art may also be used. The plasma is preferably not heat inactivated or irradiated in any way, to deactivate any possible viruses present, as this will lead to denaturing of the plasma proteins in general and the GG in particular.

Heat inactivation causes conversion of the fibrinogen in the plasma to fibrin, which settles out in the plasma in the form of particles ranging in size from small flakes, to large "jelly" clots. This renders it impossible to transfuse through a filtered giving set, and indeed harmful if infused without a filtered giving set.

The method of the invention results in the production of sterile (free of contamination by bacteria, fungi, yeast, and virus), pure plasma of stated (high) potency. Accordingly, plasma made in accordance with the present invention comprises the following preferred characteristics:

Sterility—tested by incubation of samples of plasma from every batch produced. The media are Thioglycollate Broth, which tests for anaerobic bacteria, and Tryptone Soy Broth, which tests for aerobic bacteria and yeast and fungi. Results of Sterility Testing on all ten batches of canine plasma produced are tabulated in Table 4.

Purity—this is an indication of the amounts of contaminating blood cells that are present in the plasma. There are thresholds for red cells, white cells and platelets, above which the plasma is unacceptable for use/sale. These preferred maximum levels are: red cells—30,000 million/L of plasma, white cells—200 million/L of plasma and platelets—50,000 million/L of plasma.

Potency—as stated previously, the minimum Gamma Globulin concentration that is preferably acceptable is 10 g/L. This parameter is measured by the Canine Radial Immunodiffusion Test (Triple J Farms, USA).

Quality control results of 10 batches of Canine plasma produced are shown in Table 4. All of these dogs were dogs of unknown health history (although a veterinary clinical examination before plasmapheresis revealed no abnormality), which were destined for euthanasia. They were euthanased the day after their collection, once it was noted that they recovered from the anaesthesia and the plasmapheresis without any ill effects. None of them received any immunizations, and no other effort was made to boost GG concentrations before collection. However, donor number 1 was administered limited hyperimmunization and samples are shown in batches 4, 7, 8, 9 and 10 (see Table 4). As shown in Table 4, hyperimmunization generally increased GG levels.

Plasma Collection Method

Figure 3:
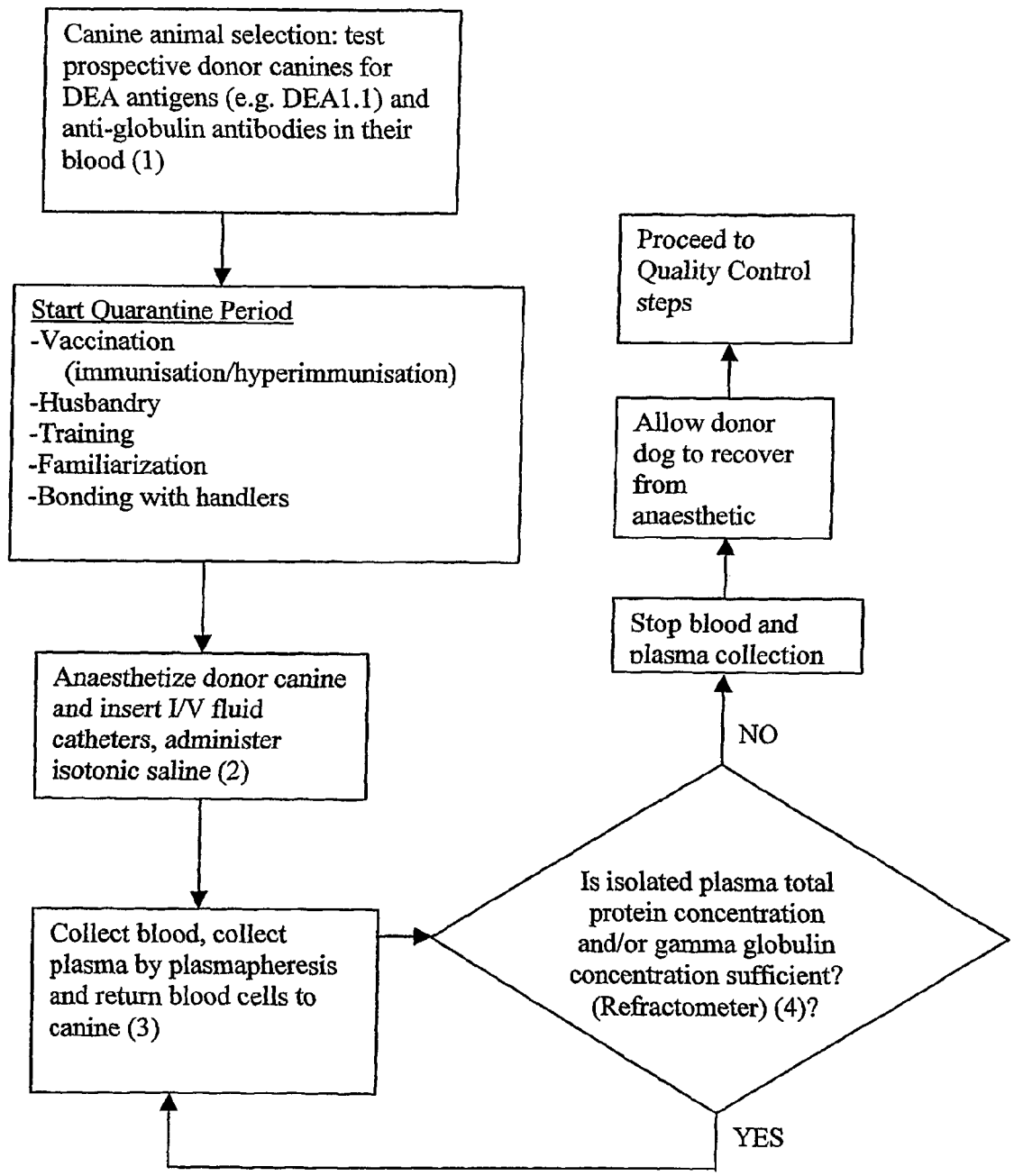
FIG. 3 is a flow diagram showing steps of a preferred method of canine plasma isolation.

FIG. 3 shown a flow chart of the plasma isolation process, indicating the points at which the various in-process tests are carried out. (1) selecting and testing of prospective donor dogs for suitability as plasma donors, by the Rapid Vet H card test for Dog Erythrocyte Antigen 1.1, and testing those dogs which are negative, to the Coomb's Test as described herein. Dogs which are negative to both tests are then selected as plasma donors. The selected donors may be immunized or hyperimmunised as described herein. (2) monitoring of the level of anaesthesia, by means of the use of an oesophageal stethoscope—carried out by Technician, by the observation of certain set parameters, and their predetermined upper and lower limits, under the supervision of a Veterinarian, see table 5. (3) observation by Technician that the amount of plasma collected per "draw" cycle is decreasing rapidly—once cycle volume falls below 50 mL per cycle, discontinue collection at the end of that bag. As described herein, blood is collected, plasma is collected from the blood by separating the plasma and blood cells and the blood cells are returned to the canine. (4) measure Total Protein concentration and/or gamma globulin concentration of the small quantities of the isolated plasma in the discarded plasma filling lines of the Transfer bags—once TP falls below 25 g/L and/or gamma globulin falls below 10 g/L, discontinue collection at the end of that bag. The isolated plasma preferably comprises at least 25 g/L total protein or at least 10 g/L gamma globulin. If the TP or gamma globulin concentrations are within acceptable values, plasma collection continues. After the plasma collection is stopped, the donor dog is allowed to recover and the plasma is further assessed for quality control.

Example 6

Monitoring the Level of Anaesthesia of the Donor Dog During Plasmapheresis

This is achieved by the application of standard veterinary anaesthetic technique, by observation of parameters, including those of Table 5. These parameters, their upper and lower limits, and remedies if outside these limits are tabulated, as shown for example in Table 5.

Measurement of Total Plasma Protein of Plasma Bag Line Samples of Plasma During Collection This is performed using a hand-held Refractometer, to measure the Total Protein (TP) concentration of the plasma. Total Protein is a measurement of the amount of protein within the plasma. Plasma Proteins exert colloidal osmotic pressure and aid in maintenance of the acid-base balance. Proteins comprise enzymes, antibodies, coagulation factors, hormones and transport substances (DUNCAN J R, PRASSE K W, and MAHAFFEY E A, "Veterinary Laboratory Medicine—Clinical Pathology" Third Edition, 1996, pages 112 and 238).

The difference between Plasma Protein and Serum Protein is that Serum Protein lacks the non-enzymatic coagulation proteins, Fibrinogen and Factors V and VIII, which are consumed in the formation of the clot.

Albumins are those proteins, which arrive in the blood stream as a result of digestion of food within the intestines, and subsequent synthesis by the liver, as well as by the result of catabolism of various tissues within the body (usually muscle). Albumins usually constitute 35-50% of TP.

Globulins are separated into three major classes by electrophoresis:

(1) alpha and (2) beta globulins, most are synthesized by the liver are the acute phase proteins and some immunoglobulins (IgM, IgA) may extend from the gamma region into the beta region; and (3) gamma globulins, most of the immunoglobulins are in this group
are secreted by the B lymphocytes and plasma cells in many tissues, particularly the lymphoid organs By subtraction, globulins are usually 50-65% of TP. The normal values, for the various globulins, as quoted by the above authors, are shown in Table 6.

This constant relationship of the GG to TP (in the normal, healthy dog) enables reasonably confident, therefore, in the existence of a constant, proportional relationship between gamma globulins and TP. This can be summarized by the following results of testing shown in Table 7. Neither the "split filling" nor reservoir bag techniques were performed on any of these batches Measurement of Total Protein (TP) of plasma bag line samples of plasma during collection is shown in table 7. The values of table 7 only apply to the healthy animal. In any animal suffering from an infection, GG values will be markedly (and unpredictably) elevated, due to the antigen/antibody response of the host to the infection, and this proportionality will be lost and completely undeterminable (with the same ease as simply reading a Refractometer).

The nature of a relationship of TP to GG concentration varies between each species, which results in different minimum GG concentration specifications for each plasma product from the different species. Based on experience and experimentation by the inventor, a TP reading on the Refractometer of 25 g/L, equates to a minimum desired concentration of GG in plasma of 10 g/L. This finding is an integral part of the In-Process Quality Control testing procedures as it will enables prediction of when to preferably stop the collection of plasma. It has been shown that GG levels decline sharply during the collection of plasma from a dog, as shown in Table 8, which summarizes some collection data (where the "split fill" bag filling method was not used).

TP monitoring is preferably not performed on plasma as it is collected, rather on plasma emerging from the plasma bag once gently mixed. This sampling will be performed on plasma collected from the plasma line, after the process of expulsion of air bubbles from the bag.

In the same way as the TP reading was used to assess when the collection should discontinue, it will also be used as a means of determining the point at which the Technician should "turn around"—that is, stop half-filling the bags (with approximately 100 mL of plasma), and commence filling the bags (to 200 mL), in reverse order. The Refractometer reading for TP, which is use to indicate a "half-way" point is 30 g/L.

Observing the Volume of Each "Draw" Cycle

When a collection commences, approximately 200 mL of plasma is collected per cycle. This volume declines in a linear fashion during the collection, proportional to the body weight of the donor. Administration of intravenous isotonic fluids (e.g. saline) during plasma collection slows the rate of decline of "draw" cycle volume, but, if the "draw" cycle volume declines to below 75 mL, the collection will be discontinued, once that current bag has been filled. A decline in "Draw" cycle volume to this degree is rare, because the TP reading usually falls to less than 25 g/L before this happens.

The shortening of the "draw" cycle volume may indicate that the donor is suffering from a form of "metabolic stress", for example due to reduction of the plasma pool within the blood as a result of plasma collection. This stress is also usually accompanied by some degree of haemolysis, and the plasma starts to turn slightly pink in colour. When this occurs, despite the supplementation of blood volume by the Intravenous Isotonic fluids, the collection preferably is discontinued.

It is thought by us that the haemolysis is the result of red cell damage to the cell walls by the amount of centrifugation of the blood that occurs in the course of the collection. This phenomenon has not been observed in any of the other of the 3 species, from which we have collected plasma in our time in the business.

In the process of building canine plasma stocks, by collection from "Pound" dogs, destined for euthanasia, but known to be in good health, the recovery of dogs from whom plasma was taken after their "draw" cycle volume fell below 75 mL, was closely monitored. No abnormality was noted, in the 24 hours following recovery from the anaesthetic, in any such dogs.

Example 7

Collection of Retention Samples During the Course of the Collection

Five such samples are usually collected during a collection. The first sample is collected as soon as clear, non-milky plasma starts to flow on the first cycle. The milky plasma is collected in the "dump" or "Platelet" bag, and as soon as it becomes clear, it is collected into the plasma bag. This sample is assessed for cell counts, preferably by an independent laboratory. The final (fifth) sample is the last plasma drawn from that collection. This sample is used for the Sterility Testing for Aerobic and Anaerobic bacteria (because any build up of bacterial contamination would be at its highest, the longer the collection progresses), and for GG concentration, because the final bag filled contains the weakest plasma, and it is essential that all bags meet the minimum specification of 10 g/L GG. The other three samples are collected at intervals of every two cycles, and are kept in frozen storage until one year after the expiry of the shelf life granted by the NRA on this application—argued previously as being three years. The radial immunodiffusion tests have evolved from the work of Fahey and McKelvey (Fahey and McKelvvey, 1965, J Immunol 94 84). They are specific for the various proteins in serum or other fluids and depend on the reaction of each protein with its specific antibody. When the wells in the antibody comprising gel are completely filled with the antigen, the precipitin rings, which develop after 10-20 hours at room temperature are measured. The diameter of the ring and the logarithm (base 10) of the protein concentration are related in a linear fashion. Using appropriate reference standards, the concentration of unknown samples may be measured." Preferably, a testing product available from TRIPLE J FARMS (23404 North East 8th Street, Redmond, Wash. 98053 USA) is used. If allowed to proceed to "end point" the relationship between GG concentration and the radius of diffusion can be plotted in a linear fashion, rather than logarithmic, and this "end point" is usually reached after some 36 to 48 hours, when all diffusion has finished. The Radial Immunodiffusion (RID) Test is quantitatively accurate, reasonably simple to perform, repeatable and a minimally expensive means of measuring GG concentrations.

As stated in the instructions enclosed with the RID test plates, the test can be completed in as little as eight hours, as long as the test samples are read at the same time as the Control samples each and every time tests are performed. If the operator chooses, or is unable to do so sooner, the test can be read at "end point" (ie when the diffusion has proceeded as far as it can go)—usually after 32-48 hours.

References to the use of the RID test for measurement of GG levels in foal serum, as a means of diagnosis of FPT in foals has been previously described, for example, McKinnon and Voss, 1993, "Equine Reproduction", Lea & Febiger, Chapter 111 "The Immune System", page 1008; Leblanc, 1990, "Equine Clinical Neonatology", Lea & Febiger Immunologic Considerations, page 284; JEFFCOTT, "Current Therapy in Equine Medicine 2", WB Saunders Company (1987), "Passive Transfer of Immunity to Foals", page 214; WHITE, Address to the Department of Large Animal Medicine, College of Veterinary Medicine, University of Georgia, Athens, Ga. USA, "The Use of Plasma in Foals With Failure of Passive Transfer and/or Sepsis", page 217; LEBLANC and ASBURY, Equine Veterinary Science, Vol 5, Number 2, "Treatment of Foals with Failure of Passive Transfer using Plasma obtained by Plasmapheresis", page 79; VAALA, "Equine Stud Medicine", Proceedings of the Post Graduate Foundation in Veterinary Science, University of Sydney (1996)—Section on "Failure of Passive Transfer: Diagnosis, Treatment and Prevention" pages 33-34; BLOOD and RADOSTITS, "Veterinary Medicine" seventh edition (1989)—Diseases of the Newborn page 113), each of the preceding incorporated herein by reference.

Sterility Testing of Canine Plasma

A test is described by the United States Department of Agriculture (UNITED STATES DEPARTMENT OF AGRICULTURE—SAM 900 and SAM 902, 9 Mar. 1978), utilizes steamed tubes of Thioglycollate broth (for anaerobic bacteria), and tubes of Tryptone Soy broth (aerobic bacteria). The former is incubated at 35 degrees Centigrade for 14 days, and the latter at room temperature for 14 days. Two plasma tubes and one control tube are utilized. After the incubation period, one of the plasma tubes is then tested for "fertility" by infusing the contents with a known contaminant, and watching for strong growth within 2 days. In addition, operator technique is validated, by the incubation of the Latham Bowl, filled with steamed Thioglycollate broth and sealed at inlet and outlet, and incubated for 14 days, from each of three consecutive collections by one technician, per year, per animal form which the Technician collects plasma.

Autoanalysis is performed using standard pathology laboratory technique. The limits of sensitivity of the Coulter STKS Autoanalyser (as quoted by the machine manual, as appears on the Result Sheets enclosed) are as follows:—Red Blood Cells—30,000 million per liter, White Blood Cells—200 million per liter and Platelets—10,000 million per liter A minimal acceptable levels of cell contamination allowable in fresh frozen plasma used for plasma therapy in humans, according to the European Council on Plasmapheresis (European Council on Plasmapheresis, "Guide to Preparation, use and quality assurance of blood components, New Edition, Council of Europe Press, 1995), are: Red Blood Cells—6,000 million per liter, White Blood Cells—100 million per liter and Platelets—50,000 million per liter.

All plasma samples tested were within acceptable limits.

Plasma samples are tested using the *Limulus* Amoebocyte Inhibition Lysate (LAL) test (BIOTEST LABORATORIES PTY LTD, Underwood, Australia). This test is also performed detects the presence of pyrogens, the most important of which is endotoxins.

Example 8

Clinical Cases Receiving Plasma

Fourteen dogs, all of which could be classified as being acutely, severely ill, received transfusions of non-immune plasma made in accordance with the present invention. These cases are summarized in tables 9 and 10. In table 10, the (*) refers to case 14, which was counted as both Pancreatitis and Parvovirus/Enteritis (because there was evidence of both disorders being present). The term "success" and "successful outcome" are defined as a dramatic improvement, which was judged to have: resulted in a much shorter period of hospitalization, resulted in a much shorter course of medication, which was also prescribed for the patient, actually saved the life of a patient which would otherwise have died, and/or any combination of the above.

To summarize, cases numbered 3, 5, 6, 7, 8, 10, 12, 13 and 14 all received considerable benefit from the plasma therapy administered during the course of their illness. In some cases, the plasma therapy was a difference between life and death.

It is understood that the invention described in detail herein is susceptible to modification and variation, such that embodiments other than those described herein are contemplated which nevertheless falls within the broad scope of the invention.

The disclosure of each patent and scientific document, computer program and algorithm referred to in this specification is incorporated by reference in its entirety.

What is claimed is:

1. A method of isolating plasma from a canine animal including the steps of:
    (I) selecting a donor canine animal having a blood group compatible with a recipient canine animal having an unmatched blood group, wherein the donor canine animal is selected for a phenotype lacking anti-globulin antibodies;
    (II) collecting blood from the donor canine animal after administering a heat-killed *E. coli* antigen to said donor canine animal; and
    (III) isolating plasma from blood collected in step (II).

2. The method of claim 1 wherein the donor canine animal is selected for a phenotype lacking at least one Dog Erythrocyte Antigen.

3. The method of claim 2 wherein the donor canine animal is negative for Dog Erythrocyte Antigen 1.1.

4. The method of claim 3 wherein the donor canine animal is negative for Dog Erythrocyte Antigen 1.2.

5. The method of claim 4 wherein the donor canine animal is negative for Dog Erythrocyte Antigen 7.

6. The method of claim 1 wherein step (II) further includes the steps of:
    (a) inserting a blood collecting catheter into a vein of the donor canine animal;
    (b) attaching the blood collecting catheter to a cell separator capable of separating blood into an isolated plasma component and an isolated blood cell component;
    (c) collecting blood from the donor canine animal via the blood collection catheter;
    (d) separating the blood into the isolated plasma component and the isolated blood cell component;
    (e) collecting the isolated plasma component;
    (f) stopping the collecting of blood;
    (g) returning the blood cell component to the donor canine animal; and
    (h) repeating steps (c)-(g).

7. The method of claim 1, wherein said heat-killed *E. coli* antigen is an *E. coli* J5 antigen.

8. A method of producing hyperimmunised canine animal plasma including the steps of:
    (1) selecting a donor canine animal having a blood group compatible with a recipient canine animal having an unmatched blood group, wherein said donor canine animal is characterised by a phenotype negative for anti-globulin antibodies;

(2) administering to the donor canine animal a heat-killed *E. coli* antigen thereby inducing an immune response in said donor canine animal;

(3) administering to said donor canine animal a heat-killed *E. coli* antigen during said immune response; and (4) isolating plasma from said donor canine animal.

9. The method of claim 8 wherein said donor canine animal is further characterised by a phenotype negative for at least one Dog Erythrocyte Antigen.

10. The method of claim 9 wherein said donor canine animal is further characterised by a phenotype negative for Dog Erythrocyte Antigen 1.1.

11. The method of claim 9 wherein said donor canine animal is further characterised by a phenotype negative for Dog Erythrocyte Antigen 1.2.

12. The method of claim 9 wherein said donor canine animal is further characterised by a phenotype negative for Dog Erythrocyte Antigen 7.

13. The method of any one of claims 8-12, wherein the heat-killed *E. coli* antigen is an *E. coli* J5 antigen.

* * * * *